United States Patent [19]

Rosen et al.

[11] Patent Number: 5,489,578
[45] Date of Patent: Feb. 6, 1996

[54] SULFATED LIGANDS FOR L-SELECTIN AND METHODS OF TREATING INFLAMMATION

[75] Inventors: Steven D. Rosen; Stefan Hemmerich, both of San Francisco, Calif.

[73] Assignee: The Regents of the University of California, Oakland, Calif.

[21] Appl. No.: 432,849

[22] Filed: May 2, 1996

Related U.S. Application Data

[63] Continuation of Ser. No. 155,947, Nov. 19, 1993, abandoned.

[51] Int. Cl.$^6$ .......................... A61K 37/20; A61K 31/70; A61K 37/02; A61K 39/00
[52] U.S. Cl. .................. 514/61; 514/25; 514/53; 514/54; 514/62; 536/4.1; 536/17.2; 536/18.7; 536/53; 536/54; 536/55.1; 536/55.2; 536/55
[58] Field of Search .................. 514/25, 53, 54, 514/62, 61; 536/4.1, 17.2, 18.7, 53, 54, 55.1, 55.2, 55

[56] References Cited

U.S. PATENT DOCUMENTS 5,143,712   9/1992   Brandley et al. ................ 424/1.73

FOREIGN PATENT DOCUMENTS 9119502   12/1991   WIPO.

OTHER PUBLICATIONS

Green et al., *Biochem. Biophys. Res. Commun.* 1992, 188(1), 244–251.
Suzuki et al., *Biochem. Biophys. Res. Commun.* 1993, 190(2), 426–434.
Needham et al., *Proc. Nat. Acad. Sci.* 1993, 90, 1359–1363.
Mawhinney et al., *Carbohydr Res.* 1992, 235, 179–197.
Capon et al., *Eur. J. Biochem.* 1989, 182, 139–152.

*Primary Examiner*—Douglas W. Robinson
*Assistant Examiner*—Kathleen Kahler Fonda
*Attorney, Agent, or Firm*—Fish & Richardson; Karl Bozicevic; Valeta Gregg

[57] ABSTRACT

Sulfated oligosaccharides which bind to L-selectin receptors and act as agonists are formulated into pharmaceutical formulations and administered by injection to treat inflammation. Compounds which act as metabolic inhibitors of carbohydrate sulfation and inhibit the sulfation of naturally occurring ligands for L-selectin receptors are administered locally by injection to alleviate and/or prevent inflammation. The sulfated oligosaccharides can be administered in combination with the chlorates and sulfatases in order to obtain a combined effect which is useful in preventing and/or alleviating inflammation. A preferred group of ligands are obtained by the hydrolysis of GlyCAM-1 by separation procedures including high pH anion exchange chromatography. The invention describes compounds that have the recognition determinants for L-selectin on GlyCAM-1 as Galactose-6-sulfate and/or N-acetylglucosamine-6-sulfate, in concert with sialic acid and fucose.

18 Claims, 9 Drawing Sheets

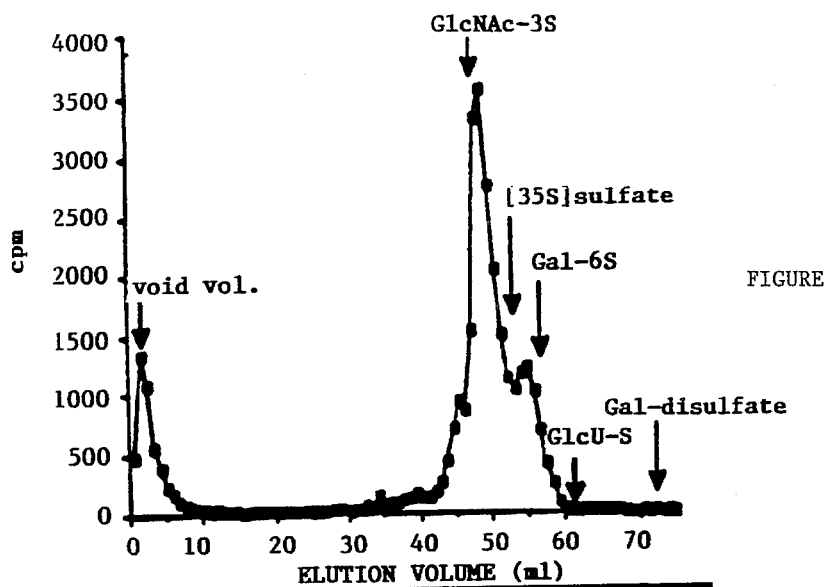
FIGURE 3A
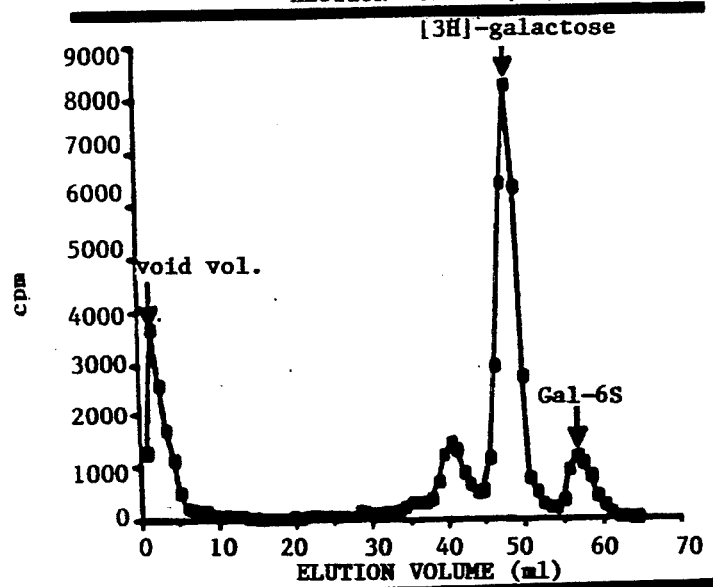
FIGURE 3B
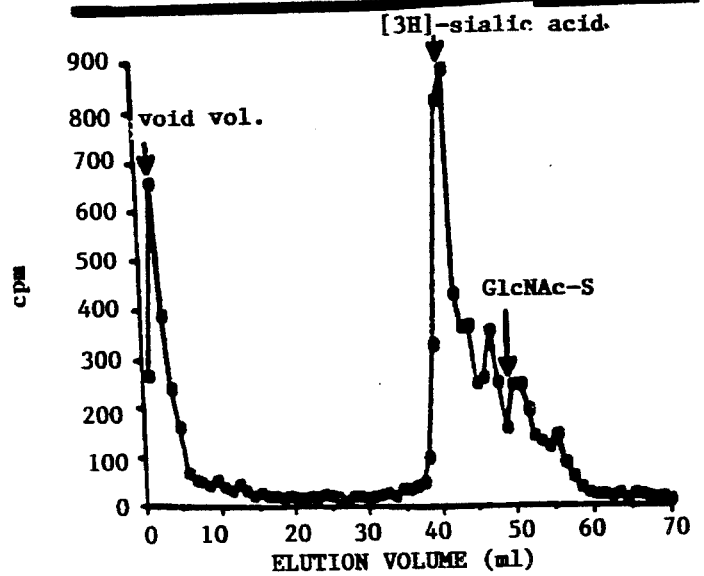
FIGURE 3C
FIGURE 3

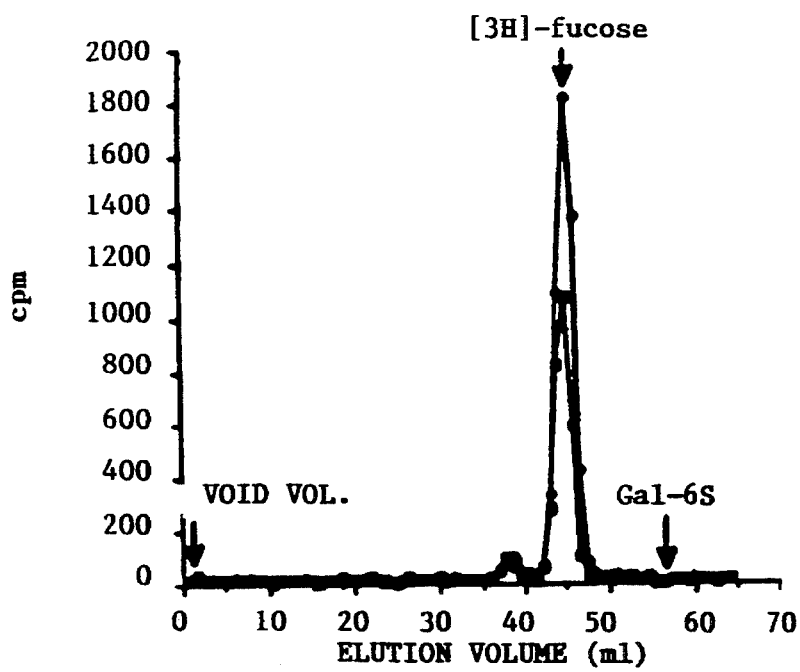
FIGURE 4A
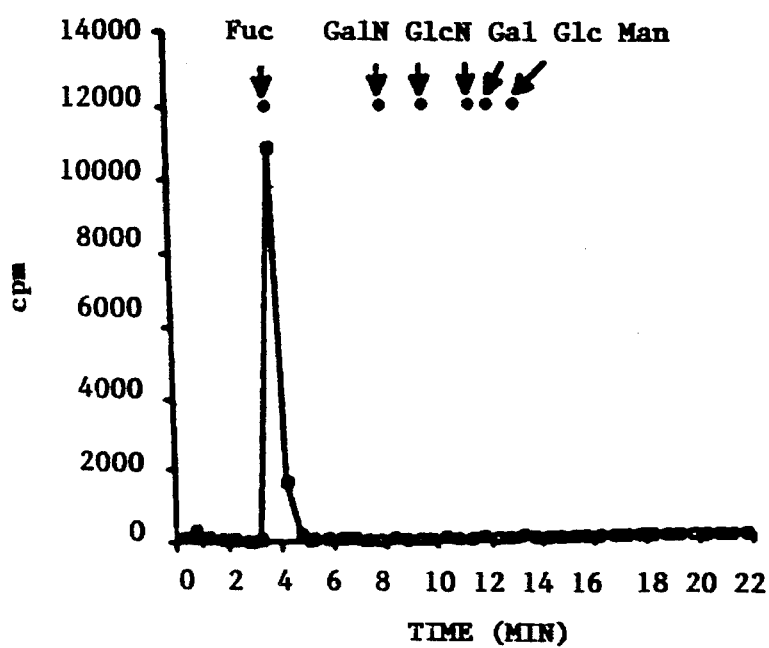
FIGURE 4B
FIGURE 4

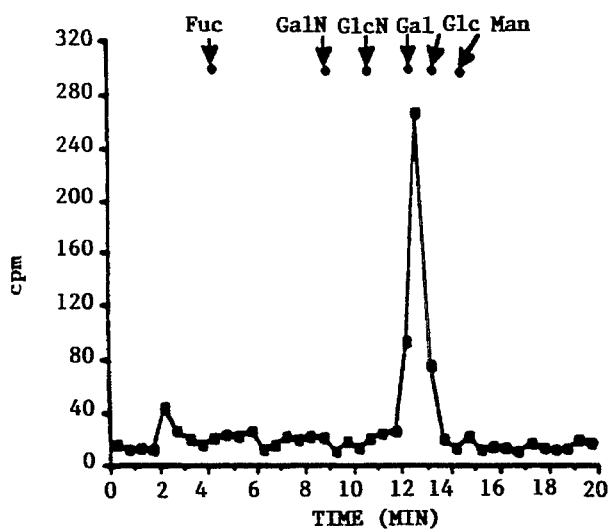
FIGURE 7A
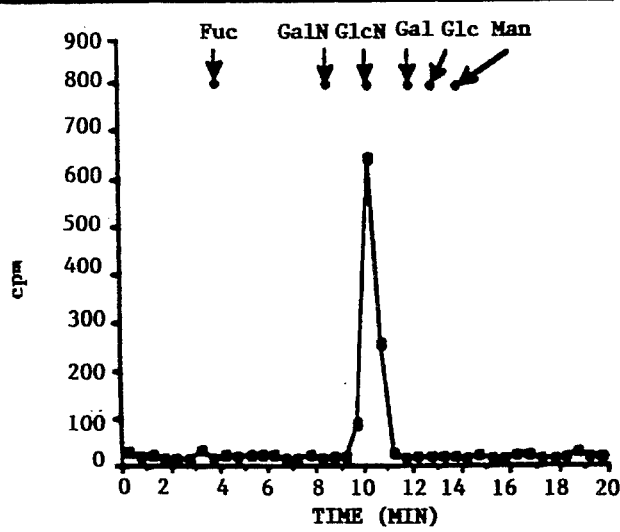
FIGURE 7B
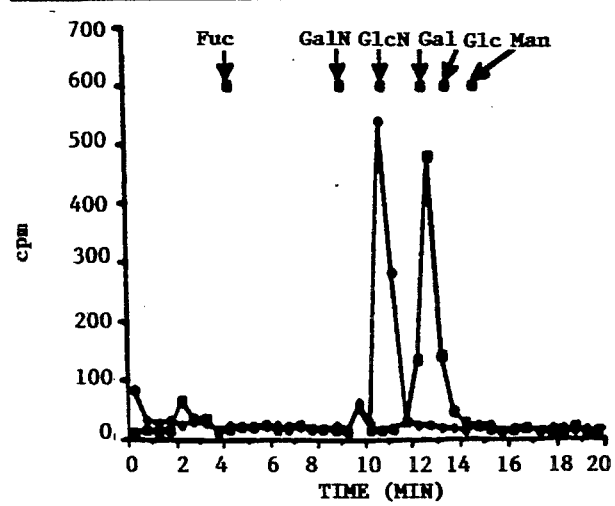
FIGURE 7C
FIGURE 7

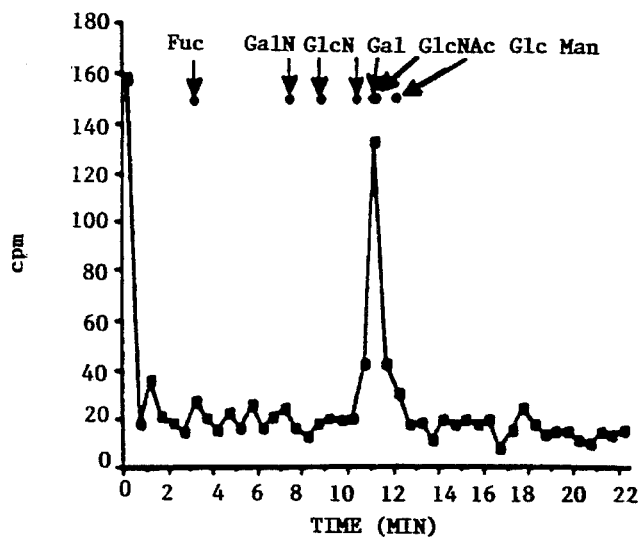
FIGURE 8A
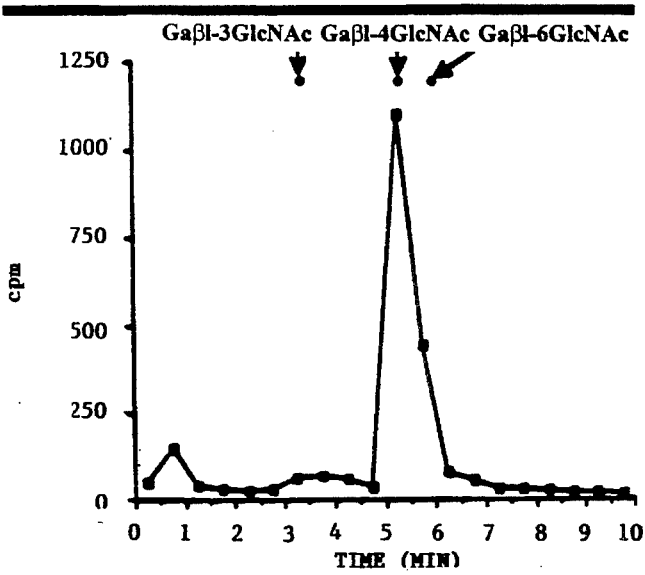
FIGURE 8B
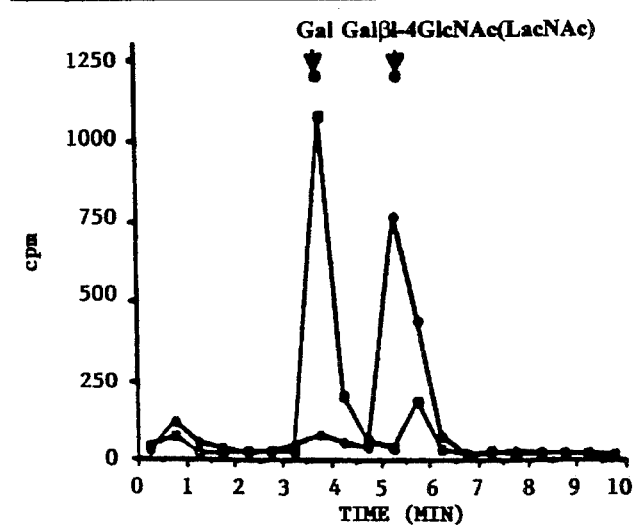
FIGURE 8C
FIGURE 8

5,489,578

SULFATED LIGANDS FOR L-SELECTIN AND METHODS OF TREATING INFLAMMATION

GOVERNMENT RIGHTS

The United States Government may have certain rights in this application pursuant to Grant No. GM-23547 awarded by the National Institute of Health.

RELATED APPLICATIONS

This application is a continuation of U.S. application Ser. No. 08/155,947 filed Nov. 19, 1993, now abandoned, which we claim priority under 35 USC § 120 and which is incorporated herein by reference.

FIELD OF THE INVENTION

The present invention relates generally to sulfated ligands and to methods of preventing the metabolic addition of a sulfate to a natural ligand or remove a sulfate to thereby prevent the attachment of the ligand to a receptor. More specifically, the invention relates to sulfated forms of O-linked oligosaccharide chains and to locally administering compounds such as non-toxic chlorates which metabolically prevent the addition of a sulfate moiety to an L-selectin ligand resulting in desirable effects such as alleviation of inflammation.

BACKGROUND OF THE INVENTION

There have been a number of research efforts investigating the role of carbohydrates in physiologically relevant recognition. (See Brandley, B. K., and Schnaar, R. L., *J. Leuk. Biol.* (1986) 40:97; and Sharon, N., and Lis, H., *Science* (1989) 246:227). Oligosaccharides are well positioned to act as recognition molecules due to their cell surface location and structural diversity. Many oligosaccharide structures can be created through the differential activities of a smaller number of glycosyltransferases. Their diverse structures, then, can be generated with relatively few gene products, suggesting a plausible mechanism for establishing the information necessary to direct a wide range of cell-cell interactions. Examples of differential expression of cell surface carbohydrates and putative carbohydrate binding proteins (lectins) on interacting cells have been described (see Dodd, J., and Jessel, T. M., *J. Neurosci.* (1985) 5:3278; Regan, L. J., et al., *Proc. Natl. Acad. Sci. USA* (1986) 83:2248; Constantine-Paton, M., et al., *Nature* (1986) 324:459; and Tiemeyer, M., et al., *J. Biol. Chem.* (1989) 263:1671). Further, the question has been raised as to the nature of the leukocyte receptor for ELAM-1 (see Bevilacqua et al. *Proc. Natl. Acad. Sci. USA* (1987) 84:9238).

Tumor associated glycolipids have been reported in fetal tissue and a variety of human cancers, including CML cells (Fukuda, M. N., et al., *J. Biol. Chem.* (1986) 261:2376; Magnani, J. L., et al., *J. Biol. Chem.* (1982) 257:14365; Hakomori, S., et al., *Biochem. Biophys. Res. Comm.* (1983) 113:791). This has led to the hypothesis that these structures may be important in many developmental and oncogenic processes (J. L. Magnani et al., *J. Biol. Chem.* (1982) 257:14365). Smaller quantities of most of these carbohydrates can be found in normal human tissue (see Fukushi, Y., et al., *J. Exp. Med.* (1984) 160:506), but until now no function for these structures has been reported.

Adhesion of circulating leukocytes to stimulated vascular endothelium is a primary event of the inflammatory response. Several receptors have been implicated in this interaction, including a family of putative lectins that includes $gp90^{MEL}$ (Leu8), GMP-140 (PADGEM) and ELAM-1 (Gong, J.-G., et al., *Nature* (1990) 343:757; Johnston, G. I., et al., *Cell* (1989) 56:1033; Geoffroy, J. S., and Rosen, S. D., *J. Cell Biol.* (1989) 109:2463; Lasky, L. A., et al., *Cell* (1989) 56:1045). All three of the presently known selectins have been shown to recognize carbohydrates (see Lasky, *Science*, 258:964–969, 1992). Endogenous ligands for these receptors are being identified.

ELAM-1 is interesting because of its transient expression on endothelial cells in response to IL-1 or TNF (Bevilacqua, M. P., et al., *Science* (1989) 243:1160). The time course of this induced expression (2–8 h) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding the ELAM-1 receptor.

Recently, several different groups have published papers regarding ELAM-1 ligands which are also referred to as LECAM-2 ligands. Lowe et al. (1990) demonstrated a positive correlation between the LECAM-2 dependent adhesion of HL-60 cell variants and transfected cell lines, with their expression of the sialyl Lewis X ($sLe^x$) oligosaccharide, Neu NAc α2–3Gal-β1–4(Fuc α1–3)-GlcNAc and generally shown more specifically as Siaα2–3Galβ1–4[Fucα1–3]-GlcNAc. By transfecting cells with plasmids containing an α(1,3/1,4) fucosyltransferase, they were able to convert non-myeloid COS or CHO lines into $sLe^x$-positive cells that bind in an LECAM-2 dependent manner. Attempts to block LECAM-2 dependent adhesion using anti-$sLe^x$ antibodies were uninterpretable due to the agglutination of the test cells by the antibody. They conclude that one or more members of a family of oligosaccharides consisting of sialylated, fucosylated, lactosaminoglycans are the ligands for the lectin domain of LECAM-2. Phillips et al. (1990) used antibodies with reported specificity for $sLe^x$ to inhibit the LECAM-2 dependent adhesion of HL-60 or LEC11 CHO cells to activated endothelial cells. Liposomes containing difucosylated glycolipids with terminal $sLe^x$ structures inhibited adhesion, while those containing non-sialylated Lex structures were partially inhibitory. Walz et al. (1990) were able to inhibit the binding of a LECAM-2-lgG chimera to HL-60 cells with a monoclonal antibody directed against $sLe^x$ or by glycoproteins with the $sLe^x$ structure, but could not demonstrate inhibition with CD65 or CD15 antibodies. Both groups concluded that the $sLe^x$ structure is the ligand for LECAM-2.

Information regarding the DNA sequences encoding endothelial cell-leukocyte adhesion molecules are disclosed in PCT published application WO90/13300 published Nov. 15, 1990. The PCT publication cites numerous articles which may be related to endothelial cell-leukocyte adhesion molecules. The PCT publication claims methods of identifying ELAM-ligands, as well as methods of inhibiting adhesion between leukocytes and endothelial cells using such ligands and specifically refers to MILAs which are described as molecules involved in leukocyte adhesion to endothelial cells.

LECAM-1 is interesting because of its involvement in lymphocytic and neutrophil influx (Watson et al., *Nature*, 349:164–167 (1991)). It was expressed in chronic lymphocytic leukemia cells which bind to HEV (see Spertini et al.,

*Nature*, 349:691–694 (1991)). It is believed that HEV-like structures at sites of chronic inflammation are associated with the symptoms of disease such as rheumatoid arthritis, psoriasis, and multiple sclerosis.

A broad range of ELAM-1 ligands are disclosed in PCT/US91/05416 published as WO 92/02527 (published 20 Feb. 1992) to Brandley et al. and in PCT/US90/02357 published as WO 90/13300 (published 15 Nov. 1990) to Hession et al. both of which are incorporated herein by reference in their entirety and specifically to disclose oligosaccharide structures which reportedly act as ELAM-1 and LECAM-1 ligands.

The selectins are a family of three cell-cell adhesion proteins that mediate various leukocyte-endothelial adhesion events (reviewed in Lasky, L. A., *Science*, 258:964–969 (1992); McEver, R. P., *Curr. Opin. Cell Biol.* 4:840–849 (1992); Bevilacqua, M. P., and Nelson, R. M., *J. Clin. Invest.*, 91:379–387 (1993); Rosen, S. D., *Semin. in Immunol.*, 5:237–249 (1993). L-selectin is expressed on the surface of leukocytes and participates in the homing of blood borne-lymphocytes to peripheral lymph nodes (Gallatin, W. M., Weissman, I. L., and Butcher, E. C., *Nature*, 903:30–34 (1983); Geoffroy, J. S., and Rosen, S. D., *J. Cell Biol.*, 109:2463–2469 (1989)) by mediating attachment to the specialized endothelial lining cells of high endothelial venules (HEV). L-selectin, a lectin-like receptor bearing a calcium-type domain, mediates the attachment of lymphocytes to high endothelial venules (HEV) of lymph nodes (Gallatin et al., *Nature*, 303:30–34 (1983); Lasky, L. A., *Science*, 258:964–969 (1992); and Bevilacqua et al., *J. Clin. Invest.*, 91:370–387 (1993)). L-selectin is also involved in the rolling interaction of neutrophils with venular endothelium at certain sites of acute inflammation (Lewinsohn et al., *J. Immunol.*, 138:4313–4321 (1987); Ley, K., Gaehtgens, P., Fennie, C., Singer, M. S., Lasky, L. A., and Rosen, S. D., *Blood*, 77:2553–2555 (1991); Von Adrian, U., Chambers, J. D., McEvoy, L. M., Bargatze, R. F., Arfors, K. E., and Butcher, E. C., *Proc. Natl. Acad. Sci. USA*, 88:7538–7542 (1991)), an essential step for the ultimate extravasation of the leukocyte. The other two selectins, E- and P-, are expressed on endothelial cells where they mediate attachment to neutrophils, monocytes and specific subsets of lymphocytes. L-selectin participates in the entry of lymphocytes and monocytes into sites of chronic inflammation (Dawson et al., *Eur. J. Immunol.*, 22:1647–1650 (1992), and Spertini et al., *J. Exp. Med.*, 175:1789–1792 (1992)). The selectins perform their adhesive functions by virtue of C-type lectin domains at their amino termini (Drickamer, K., *J. Biol. Chem.*, 263:9557–9560 (1988)). Reflecting a high degree of sequence similarity among these domains (60–70%), the biological ligands for L-selectin on HEV and for E- and P-selectin on leukocytes share a requirement for sialic acid (reviewed in Varki, A. *Curr. Opin. Cell Biol.*, 4:257–266 (1992)). Moreover, each selectin is capable of recognizing sialyl Lewis X [sLe$^x$, i.e., NeuSAC$\alpha$2→3Gal$\beta$1→4(Fuc$\alpha$1→3)/GlcNAc] and related structures (reviewed in Stoolman, L. M., *Cell Surface Carbohydrates and Cell Development*, pp. 71–97 (1992) (M. Fukuda, ed.) CRC Press, Boca Raton, Fla.), although inhibition studies indicate that these compounds have a low binding affinity. There is evidence, based on the use of carbohydrate-specific antibodies, that sLe$^x$-related structures are present in the actual biological ligands of the selectins (Phillips, M. L., Nudelman, E., Gaeta, F., Perez, M., Singhal, A. K., Hakomori, S., and Paulson, J. C., *Science*, 250:1130–1132 (1990); Walz,. G., Aruffo, A., Kolanus, W., Bevilacqua, M., and Seed, B., *Science*, 250:1132–1135 (1990); Polley, M. J., Phillips, M. L., Wayner, E., Nudelman, E., Singhal, A. K., Hakomori, S., and Paulson, J. C., *Proc. Natl. Acad. Sci. USA*, 88:6224–6228 (1991); Berg, E. L., Yoshino, T., Rott, L. S., Robinson, M. K., Warnock, R. A., Kishimoto, T. K., Picker, L. J., and Butcher, E. C., *J. Exp. Med.*, 174:1461–1466 (1991); Sawada, M., Takada, A., Ohwaki, I., Takahashi, N., Tateno, H., Sakamoto, J., and Kannagi, R., *Biochem. Biophys. Res. Commun.*, 193:337–347 (1993); Nogard, K. E., Moore, K. L., Diaz, S., Stults, N. L., Ushiyama, S., McEver, R. P., Cummings, R. D., and Varki, A., *J. Biol. Chem.*, 268:12764–12774 (1993)). Nonetheless, each selectin has a set of preferred biological ligands (Larsen, G. R., Sako, D., Ahern, T. J., Shaffer, M., Erban, J., Sajer, S. A., Gibson, R. M., Wagner, D. D., Furie, B. C., and Furie, B., *J. Biol. Chem.*, 267:11104–11110 (1992) Berg, E. L., Magnani, J., Warnock, R. A., Robinson, M. K., and Butcher, E. C., *Biochem Biophys. Res. Commun.*, 184:1048–1055 (1992)), although information is lacking on what distinguishes the ligands of one selectin from those of another.

Presently, the best characterized ligands are the HEV-associated ligands for L-selectin, known as GlyCAM-1 (previously termed Sgp50) and Sgp90 (Imai, Y., Singer, M. S., Fennie, C., Lasky, L. A., and Rosen, S. D., *J. Cell Biol.*, 113:1213–1221 (1991)). These endothelial-associated ligands are mucin-like glycoproteins with sulfated, sialylated and fucosylated O-linked oligosaccharide chains and were originally detected by precipitation of lymph node extracts, metabolically labeled with $^{35}SO_4$, with a soluble L-selectin/immunoglobulin chimera. Other lower affinity ligands may exist that fail to be precipitated by the chimera but nonetheless participate in functionally significant interactions in the context of cell-cell binding events (Berg, E. L., Robinson, M. K., Warnock, R. A., and Butcher, E. C. *J. Cell. Biol.*, 114:343–349 (1991)). GlyCAM-1 is released into conditioned medium of cultured lymph nodes as an intact molecule (Lasky, L. A., Singer, M. S. Dowbenko, D., Imai, Y., Henzel, W. J., Grimley, C., Fennie, C., Gillett, N., Watson, S. R., and Rosen, S. D., *Cell*, 69:927–938 (1992); Brustein, M., Kraal, G., Medius, R. E., and Watson, S. R., *J. Exp. Med.*, 176:1415–1419 (1992)), suggesting that it is a secreted product and/or a loosely associated peripheral membrane component. In contrast, Sgp90 is an integral membrane protein, requiring detergent for extraction (S. Hemmerich and S. Rosen, unpublished results). Molecular analysis has revealed GlyCAM-1 to be a novel mucin-like glycoprotein, and more recently Sgp90 has also been shown to be an HIV-specific glycoform of the mucin CD34, Baumhueter, S., Singer, M. S., Henzel, W., Hemmerich, S., Renz, M., Rosen, S. D. and Lasky, L. A., *Science*, 262:436–438 (1993). GlyCAM-1 and Sgp90 are sulfated, fucosylated, and sialylated glycoproteins (Imai, Y., and Rosen, S. D., *Glycoconjugate J.*, 10:34–39 (1993)). The O-linked chains of GlyCAM-1 have been shown to be heterogeneous in both size and charge. Some of the chains bear multiple charges, the major contribution apparently coming from sulfation rather than sialylation. The interaction of both GlyCAM-1 and Sgp90 with L-selectin depends on their sialylation, confirming earlier findings that sialidase treatment of lymph node HEV impairs lymphocyte attachment and lymphocyte trafficking (Rosen, S. D., Singer, M. S., Yednock, T. A., and Stoolman, L. M., *Science*, 228:1005–1007 (1985); Rosen, S. D., Chi, S. I., True, D. D., Singer, M. S., and Yednock, T. A., *J. Immunol.*, 142:1895–1902 (1989)). However, exhaustive desialylation does not completely abrogate-the ligand activity of GlyCAM-1, suggesting that a sialic acid-independent mode of recognition also exists (Imai, Y., Lasky, L. A., and Rosen, S. D. *Glycobiology*, 4:373–381). The sialic acid which forms part of the ligand binding site of GlyCAM-1 appears to be in an α2→3 linkage, since the linkage-specific sialidase from Newcastle disease virus partially inactivates GlyCAM-1 as a ligand. Furthermore, both in competitive inhibition studies and direct binding studies, sLe$^x$-type oligosaccharides manifest ligand activity for L-selectin whereas the Lewis X-type structures with α2→6 linked Neu5Ac are inactive (Foxall, C., Watson, S. R., Dowbenko, D., Fennie, C., Lasky, L. A., Kiso, M., Hasegawa, A., Asa, D., and Brandley, B. K., *J. Cell Biol.*, 117:895–902 (1992)). An essential contribution from fucose is suspected, since sialyllactose (i.e., Neu5Acα2→3Galβ1→4Glc) as compared to sLe$^x$ is relatively inactive as a competitor of L-selectin binding. Moreover, fucose has been shown to be a critical determinant for the neutrophil ligands for P- and E-selectin (Larsen, G. R., Sako, D., Ahern, T. J., Shaffer, M., Erban, J., Sajer, S. A., Gibson, R. M., Wagner, D. D., Furie, B. C., and Furie, B., *J. Biol. Chem.*, 267:11104–11110 (1992)), and in light of the sequence similarity among the lectin domains of the selectins is likely to be important for L-selectin ligands as well.

The earlier studies have largely focused on which oligosaccharide compounds can act as ligands. In our earlier work, it was determined that attachment of a sulfate moiety to the oligosaccharide compound has a significant effect on the ability of the compound to act as a ligand and thereby developed the invention upon which copending application Ser. No. 07/943,817, filed Sep. 11, 1992, and incorporated herein by reference, was based (see also Imai, Y. and Rosen, S. D., *Glycoconjugate J.*, 10:34–39 (1993); Smai, Y., Lasky, L. A. and Rosen, S. D., *Nature*, 361:555–557. Evidence has been presented that sialyl Lewis X-related oligosaccharides, i.e.,

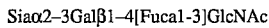

Siaα2–3Galβ1–4[Fucα1-3]GlcNAc have ligand activity, albeit very weak, for L-selectin (Foxall et al., *J. Cell Biol.*, 117:895–902 (1992), Berg et al., *Biochem. Biophys. Res. Comm.*, 184.:1048–1055 (1992), and Imai et al., *Glycobiology*). Based on studies with a carbohydrate-directed antibody, evidence also exists that endogenous HEV-ligands actually possess sialyl Lewis X-related structures (Sawada, M., *Biochem. Biophys. Res. Comm.*, 193:337–347 (1993)). Various sulfated carbohydrates including sulfatide, fucoidin (Imai et al., *J. Cell Biol.*, 111:1225–1232 (1990), related glycolipids (Suzuki et al., *Biochem. Biophys. Res. Comm.*, 190:426–434 (1993) and a sulfated form of Lewis X/a (Green et al., *Biochem. Biophys. Res. Comm.*, 188:244–251 (1992), i.e.

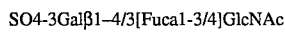

SO4-3Galβ1–4/3[Fucα1-3/4]GlcNAc have all been shown to have ligand activity for L-selectin.

The present application describes that work and provides further elaboration on the details of the carbohydrate structures which are ligands for selectins in general and L-selectin in particular, including the nature of the novel carbohydrate determinants of GlyCAM-1 involved in its recognition of L-selectin.

SUMMARY OF THE INVENTION

Novel compounds are disclosed and identified as sulfated, sialylated and fucosylated O-linked oligosaccharide chains which can be formulated with excipient carrier into pharmaceutical compositions. The compositions can be administered to a patient (preferably by injection) to treat a variety of conditions including inflammation associated with trauma and with the symptoms of diseases such as rheumatoid arthritis, psoriasis, and multiple sclerosis.

Specific ligands for L-selectin identified herein contain the following essential groups: —O$_3$SO-6-Gal, GlcNA-6-OSO$_3$—, —O$_3$SO-6-Galβ1→4GlcNAc and Galβ1→4GlcNAc-6-OSO$_3$—. Sialylated and fucosylated ligands containing these constituents can be labeled with a detectable label, such as a radioactive or fluorescent label, injected into a patient and used to identify a site of inflammation.

An object of the invention is to provide novel sulfated, sialylated and fucosylated O-linked oligosaccharide chain ligand compounds and pharmaceutical compositions comprising such ligands (which ligands can be labeled) formulated with acceptable excipient carriers.

An advantage of the invention is that the sulfated ligands can be used to effectively reduce inflammation by blocking natural receptors, acting as agonists and thereby preventing inflammation.

Yet another advantage of the invention is that a combined effect on reducing inflammation can be obtained by administering combinations of two or more of (1) a sulfated ligand agonist, (2) a compound which metabolically inhibits the addition of a sulfate moiety to a natural L-selectin ligand, and (3) an enzyme which specifically removes a sulfate moiety from a natural ligand.

A feature of the invention is that the sulfated ligands can be readily produced by sulfating known oligosaccharides using known procedures.

The sulfated ligand agonists can be bound to anti-inflammatory drugs or detectable labels and/or formulated to provide, for example, compositions useful in assaying a sample for the presence of selectin receptors, compositions useful in detecting the site of inflammation in a patient, or pharmaceutical compositions useful in treating acute inflammation (or treating the inflammatory symptoms of certain diseases) or affecting other phenomena involving the interaction of ligands and selectin receptors.

An important aspect of the invention is pharmaceutical compositions which are useful in treating, preventing and/or alleviating any undesirable effects resulting from the interaction of circulating neutrophils and endothelial cells. Such compositions are comprised of an inactive ingredient in the form of a pharmaceutically acceptable excipient material and at least one, but include one or a plurality of, sulfated ligands capable of binding to a selectin receptor.

Still another object is to provide a composition comprising a sulfated ligand which is labeled and which can be used to assay for the presence of a selectin receptor in a sample.

These and other objects, advantages and features of the present invention will become apparent to those persons skilled in the art upon reading the details of the structure, formulation and usage as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows:

FIGS. 3A, 3B and 3C are graphs of gel filtration of GlyCAM-1 mild acid hydrolysate. Parallel samples of GlyCAM-1 labeled with (3A) $^{35}SO_4$, (3B) [$^3$H]-Gal, or (3C) [$^3$H]-GlcN were hydrolyzed in 0.2M $H_2SO_4$ at 100° C. for 30 min and fractionated by Bio-Gel P4 gel filtration. The volume for the elution of the hemoglobin standard (peak fraction) is designated as the void volume. The elution volume was defined as zero at the first appearance of hemoglobin in the eluate. Thus the void volume is at 1.7 ml on this scale. The elution positions of the calibration standards are indicated with arrows;

FIGS. 4A and 4B are graphs showing the analysis of radiolabeled carbohydrate in GlyCAM-1 labeled with [$^3$H]-mannose or [$^3$H]-fucose. (4A) Parallel samples of GlyCAM-1 labeled with [$^3$H]-Man (♦), or [$^3$H]-Fuc (□) were hydrolyzed in 0.1M $H_2SO_4$ at 100° C. for 30 min and fractionated by Bio-Gel P4 gel filtration. Elution volume was defined as described in the legend to FIG. 3. (4B) Fractions encompassing the main radioactive peak (46 ml elution volume, panel a) from GlyCAM-1 hydrolysate labeled with [$^3$H]-Man were analyzed by HPAEC (20 mM NaOH isocratic). The elution time of the sample front is defined as zero. The elution times of the monosaccharide standards are indicated with arrows;

FIGS. 7A, 7B and 7C are graphs showing the monosaccharide compositions of peaks I, II, III. Singly charged fractions obtained from GlyCAM-1 mild acid hydrolysates (labeled with different precursors) were refractionated by P4 gel filtration as in FIG. 5. Peaks I, II and III were subjected to exhaustive acid hydrolysis (6 M HCl, 4 h, 100° C.) and analyzed by HPAEC (20 mM NaOH isocratic). (7A) ([$^3$H]-Gal)-labeled peak I, (7B) ([$^3$H]-GlcN)-labeled peak II, (7C) ([$^3$H]-Gal)-labeled peak III(□) and ([$^3$H]-GlcN)-labeled peak III(♦). Elution time zero was defined as in the legend to FIG. 4. The elution times of the monosaccharide standards are indicated with arrows;

FIGS. 8A, 8B and 8C are graphs showing the high pH anion exchange chromatography of desulfated peaks II and III. (8A) ([$^3$H]-GlcN)-labeled peak II and (8B) ([$^3$H]-Gal)-labeled peak III were desulfated by treatment with methanolic HCl and then analyzed by HPAEC (8A: 20 mM NaOH, isocratic; 8B: 100 mM NaOH, isocratic). (8C) A sample of desulfated ([$^3$H]-Gal)-labeled peak III was digested with jack bean exo-β-galactosidase and analyzed by HPAEC (100 mM NaOH, isocratic; □) with comparison to an undigested control sample (♦). The elution times of the carbohydrate standards are indicated with arrows.

MODES OF CARRYING OUT THE INVENTION

Figure 1:
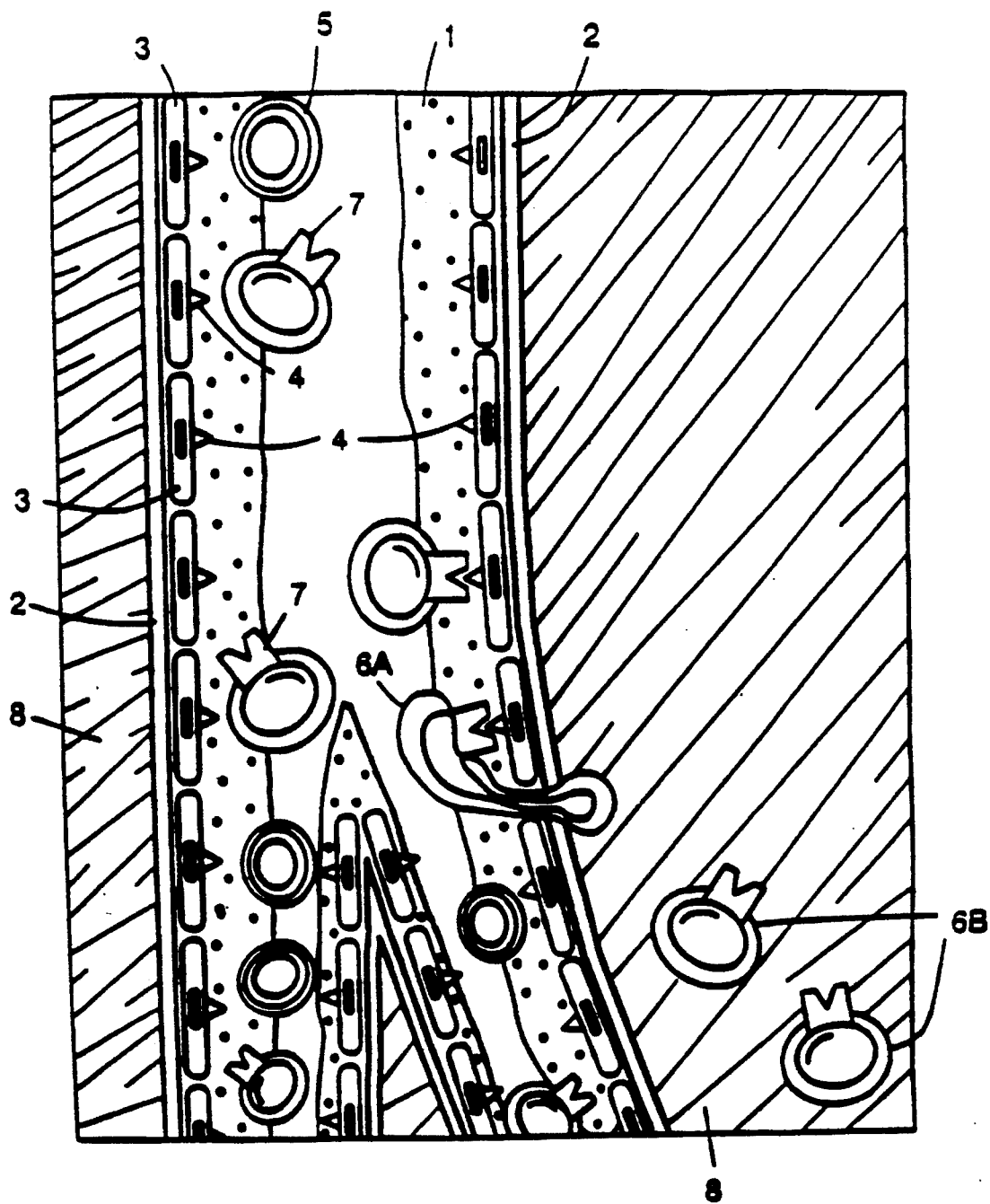
FIG. 1 is a cross-sectional schematic view showing the interaction between white blood cells and activated endothelial cells.

Before the present sulfated ligands and composition containing such ligands and processes for isolating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

As used in this specification and the appended claims, the singular forms "a", "an" and "the" include plural referents unless the context clearly dictates otherwise. Thus, for example, reference to "a sulfated ligand" includes mixtures of such ligands, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth.

All publications cited herein are incorporated herein by reference to disclosure and describe the subject matter for which they are cited in connection with.

Some standard abbreviations used in connection with the present invention include: BSA, bovine serum albumin; DEAE, diethylaminoethyl; DMSO, dimethylsulfoxide; ELAM-1, endothelial/leukocyte adhesion molecule-1 (also E-selectin); HPTLC, high performance thin layer chromatography; LECAM-1, leukocyte/endothelial cell adhesion molecule-1 (also L-selectin); MOPS, 3-[N-Morpholino]propanesulfonic acid; NANA, N-acetylneuraminic acid; PVC, polyvinylchloride; TLC, thin layer chromatography; TFA, trifluoroacetic acid; Tris, tris (hydroxymethyl) aminomethane; C-type, calcium-type; Fuc, fucose; Gal, galactose; GlcN, glucosamine; GalN galactosamine; GlcNAc, N-acetylglucosamine; GalNAc, N-acetylgalactosamine; Gal-6S, galactose-6-sulfate; GlcNAc-6S, N-acetylglucosamine-6-sulfate; GlcU-S, glucuronic acid-monosulfate; HEV, high endothelial venule; HPAEC, high pH anion exchange chromatography; LacNAc or N-acetyllactosamine, Galβ1→4GlcNAc, Man, mannose; Neu5Ac, N-acetylneuraminic acid; sialyl Lewis X or sLe$^x$, Neu5Acα2→3Galβ1→4(Fucα1→3)GlcNAc; Lewis X or Le$^x$, Galβ1→4(Fucα1→3)GlcNAc; Lewis a or Le$^a$, Galβ1→3(Fucα1→4)GlcNAc; SGNL, 3-sulfoglucuronylneolacto glycolipids; SDS-PAGE, sodium dodecylsulfate polyacrylamide gel electrophoresis, Sgp50, sulfated glycoprotein of 50 kDa; Sgp90, sulfated glycoprotein of 90 kDa.

A. General Overview

Full length naturally occurring ligands which bind to L-selectins are molecules (e.g. GlyCAM-1) far too large to be useful as pharmaceutically active drugs. However, it is possible to subject such naturally occurring ligands to digestion and obtain pieces which can be tested in assays for their ability to bind to selectins. Although a large number of pieces with different structures and chemical moieties thereon will bind to selectins some bind with greater affinity than others. We previously carried out dissection of such ligands followed by binding affinity assays to determine carbohydrates which have high binding affinity to selectins. We further determined that the ability of the ligands to bind to selectins increase substantially when the ligands included a sulfate moiety. We have now found particular sulfated ligands which have particularly high binding affinity to selectins and in particular L-selectins. We have determined the exact sulfate modifications of GlyCAM-1 and Sgp90/CD34 by direct biochemical analysis. Further, we have now subjected the sulfated ligands with the highest binding affinity to defined plant and animal lectins which have the ability to bind selectively to certain carbohydrate groups. Thus, the biological specificity of these lectins has been utilized in order to specifically determine the structure of sulfated carbohydrate ligands with particularly high binding affinity to L-selectins. In particular, we have determined the positions of sulfation which are important to obtain high binding affinity to selectins.

The present invention involves: (1) determining the monosaccharides of the GlyCAM-1 that are sulfated and further determining the positions of the sulfate substitution by direct analysis of hydrolysis products of radio-labelled GlyCAM-1 and Sgp90/CD34; (2) digesting the GlyCAM-1 with defined glycosidases; and (3) precipitating GlyCAM-1 using lectins of defined carbohydrate specificity in order to further elaborate the structure of high affinity binding portions of GlyCAM-1. As a result of carrying out these steps we have made significant advancements with respect to finding and determining the structure of small sulfated carbohydrate structures which have a high affinity for selectins and can therefore be used in binding assays for selectins and in pharmaceutical formulations in order to treat abnormalities such as inflammation. The basic sulfated carbohydrate structure is shown herein as formula I(a) and this structure may have other groups attached thereto in order to increase selectin binding affinity and/or obtain other desired results.

The ligands of the present invention preferably have certain structural features in common. Specifically, the ligands are sulfated, sialylated and fucosylated O-linked oligosaccharides comprising a recognition determinant for L-selectin which is selected from the group consisting of Galactose-6-sulfate and N-acetylglucosamine-6-sulfate. Further, the results shown here and specifically shown within tables II, III and IV demonstrate that about 35% of all galactose in GlyCAM-1 is in the penultimate position relative to sialic acid and is linked β1→4 to GlcNAc. These results also show that the fucose moiety is linked via α1→3 to GlcNAc and further that the β1→4 linked galactose residues were substituted with sulfate (preferably at the 6-position). Based on this information the preferred ligands have a capping group with the structural formula I(a)

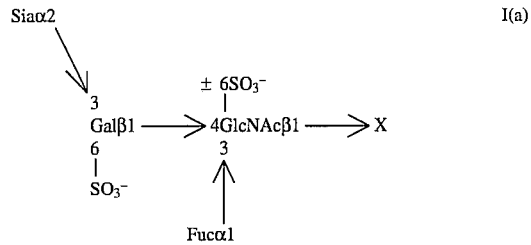

wherein GlcNAc is N-acetylglucosamine, Gal is galactose, Sia is any of the naturally occurring forms of sialic acid, Fuc is fucose, and X is any moiety connectable to the 1-position of GlcNAc. Examples of X include, but are not limited to, —OH, —O—serine-, —O-threonine, a pharmaceutically active drug such as an anti-inflammatory drug, a detectable label and the remainder of the polypeptide structure of GlyCAM-1. When X is a drug, the structure I(a) provide for specific delivery of the drug to a selectin receptor which is generally a site of inflammation. When X is a detectable label, the composition makes it possible to detect a site of inflammation. The structure I(a) includes the symbol ± with respect to the sulfate moiety which indicate here, and throughout this disclosure, that the group is optional present, i.e. use of the ± symbol means the sulfate is or is not present on all the structures where this symbol appears.

Based on studies with the lectin peanut agglutinin (PNA), in which it has been shown that desialylated GlyCAM-1 binds to this lectin, it is further established that GlyCAM-1 possesses the additional capping group shown below as structural formula I(b):

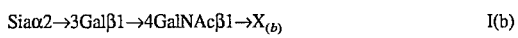

In the structure I(b), the moiety $X_{(b)}$ is defined as is X in formula I(a). However, the structure I(b) may be attached to the structure I(a) at the X position to provide for a more complete description of the GlyCAM-1 capping group as per the following structurally formula I(c):

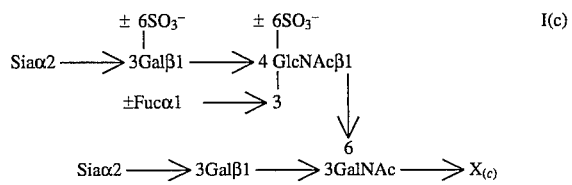

wherein $X_{(c)}$ is defined as per X in formula I(a) above.

Each of the structures I(a), I(b) and I(c) includes a sialic moiety linked to the galactose via the 3-position. We have now found an additional ligand compound which is sulfated but which does not include the sialic acid linked to the galactose via the 3-position. The structure of this ligand is shown below within general structural formula II.

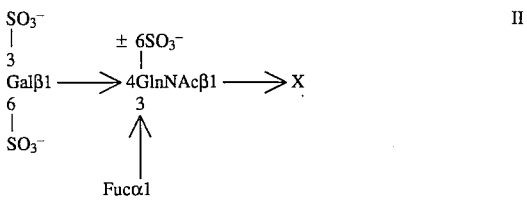

In formula II, the "X" is defined as per formula I(a) above. The structures I(d) and I(e) which are put forth below are specific structures for possible capping groups wherein the "X" is specifically defined. The "X" of general structural formula II can be defined in the same manner so as to obtain modifications of the general structural formula II which have attached to the GlcNAc at the β1-position the same moiety attached at this position on structures I(d) and I(e). Further, the presence of the symbol "±" in the above structure and all structures within this disclosure indicates that the sulfate moiety may or may not be present.

Replacement of the 3-sialylation of structure I(a) to obtain 3-sulfation in structure II is not believed to be any portion of any natural ligand. However, such a structure should provide a valuable pharmaceutically active compound (as per component 4A in FIG. 2) with high binding affinity to natural selectins. Others have shown that sialic acid can be replaced by sulfate in sialyl Lewis X with the preservation of ligand activity for both E-selectin (Yuen, C. T., Lawson, A. M., Chai, W., Larkin, M., Stoll, M. S., Stuart, A. C., Sullivan, F. X., Ahern, T. J. & Feizi, T. *Biochemistry* (1992) 31:9126–9131) and L-selectin (Green, P. J., Tamatani, T., Watanabe, T., Miyasaka, M., Hasegawa, A., Kiso, M., Yuen, C. T., Stoll, M. S., & Feizi, T. *Biochem. Biophys. Res. Commun.* (1992) 188:244–251).

With respect to all the structures disclosed and claimed herein, it should be noted that the structures are intended to encompass any and all stereoisomers of isolated and purified versions of all naturally occurring forms.

The structures I(a) and I(c) encompass sulfated, sialylated and fucosylated O-linked oligosaccharide chains of the inventions. The fucose moiety is preferably not sulfated. The compounds I(a), I(c) or II of the invention can be labeled with any detectable label and used to locate receptors or determine the location of inflammation or attached to a drug to provide for specific delivery of the drug to a selectin receptor.

The preferred ligands were analyzed with respect to the identification of any sulfated species by the hydrolysis of GlyCAM-1 followed by separation procedures as described in detail in Example 1–5. The use of glycosidases to degrade the oligosaccharide chains of GlyCAM-1, and the use of defined animal and plant lectins for binding to GlyCAM-1 also provide a group of ligands—specifically Siaα2–3Galβ1–3GalNAc-O-Ser/Thr which is extended at the 6-position of the Ser/Thr linked GalNAc. The extended structure is capped at the nonreducing terminus by a 6-sulfated, sialic Lewis X structure, i.e., terminal galactose substituted by both α2–3 linked sialic acid and sulfation at the 6-position. Some of the GlcNAc units are also sulfated at their 6-positions, i.e. compound I(c). We have identified galactose-6-sulfate and N-acetylglucosamine-6-sulfate as constituents of GlyCAM-1 which make it a particularly preferred ligand.

In addition to compounds as per the structures I(a), I(b), I(c) and II above and structures I(d) and I(e) below, the invention includes pharmaceutical formulations which contain all or any of the compounds. The invention includes a number of additional aspects such as methods of treatment using the sulfated ligands, alone or in combination with sulfatases and/or chlorates to alleviate inflammation. In order to understand the general operation of the invention, an explanation is provided below in the section entitled "In vivo Function of Ligands".

The invention also includes a method of producing, isolating and identifying the sulfated saccharides within particularly preferred L-selectin ligands which are the mild acid hydrolysis products of metabolically radiolabeled GlyCAM-1 isolated by using high pH anion exchange chromatography. The methodology includes not only subjecting GlyCAM-1 to hydrolysis and chromatography but subjecting GlyCAM-1 obtained therefrom to binding assays with defined lectins before and after treatment of GlyCAM-1 with defined glycosidases and making structural analysis deductions by bringing the fragments into contact with lectins having particularly selective activity.

In vivo Function of Ligands

FIG. 1 shows a longitudinal section view of a blood vessel 1. The vessel wall 2 is lined internally with endothelial cells 3. The white blood cells 6A and 6B can be activated causing the cells 6A and 6B to synthesize LECAM-1 which is displayed in FIG. 2 as a surface receptor 7. Both red blood cells 5 and white blood cells 6A and 6B flow in the vessel 1. The white blood cells 6A and 6B display a receptor 7 which have chemical and physical characteristics which allow the receptor 7 to bind to the ligand 4 on the endothelial cells 3. Once the receptor 7 binds to the ligand 4, a white blood cell is brought through the vessel wall 2 as is shown with the white blood cell 6A. The white blood cells 6B brought into the surrounding tissue 8 can have positive effects, such as fighting infection, and negative effects, such as inflammation. The present inventors have found that natural ligands 4 include sulfates and that (1) it is possible to inhibit the sulfation of the natural ligand by introducing a competing moiety such as a chlorate which inhibits sulfation and (2) the sulfate can be removed by the addition of a sulfatase to thereby prevent binding of the natural ligand and receptor.

Figure 2:
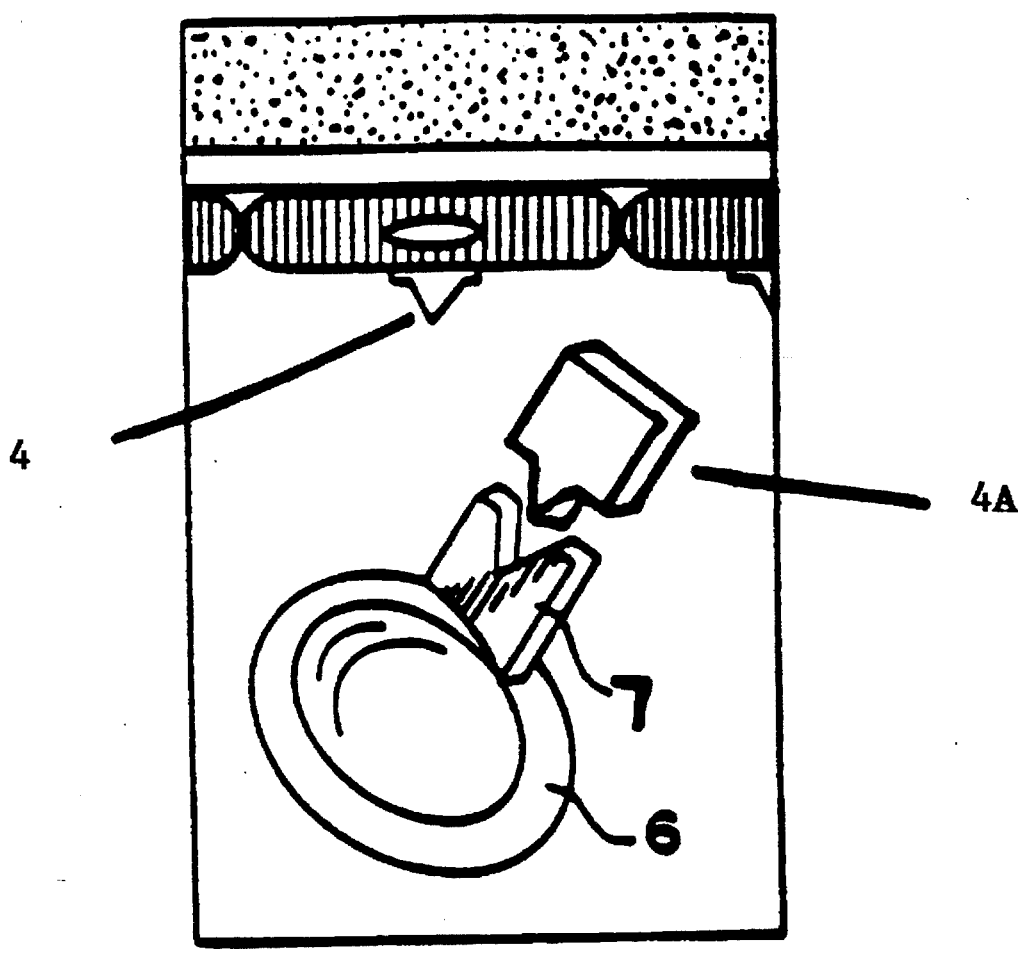
FIG. 2 is a cross-sectional schematic view showing how sulfated ligands of the invention might be used as pharmaceuticals to block L-selectin (i.e. LECAM-1)

FIG. 2 shows how a molecule 4A (representing the sulfated ligands encompassed by formulas I(a)–(e) and II of the invention) adheres to a selectin receptor 7 and can be formulated into pharmaceutical compositions, which when administered will effectively block the selectin receptor, e.g., LECAM-1 and prevent the adhesion of a receptor 7 connected to a white blood cell 6 to a natural ligand 4 on an endothelial cell 3. By administering pharmaceutically effective amounts of sulfated ligands 4A, some, but not all, of the white blood cells will not reach the surrounding tissue 8. By slowing the rate at which the white blood cells reach the surrounding tissue, inflammation can be prevented and/or alleviated.

Although it is not shown within FIGS. 1 and 2, the endothelial cells 3 also generate a receptor when correctly stimulated. This receptor can also attach to a ligand and cause adhesion between the white blood cell and the endothelial cell. Accordingly, by blocking the receptor on the endothelial cell with a synthetic ligand, it is possible to alleviate inflammation in the same manner as suggested above. To a certain extent, ELAM-1 receptors and LECAM-1 receptors will adhere to the same ligand. Accordingly, sulfated ligands of the present invention can be used to block receptors on the white blood cells and simultaneously block receptors on endothelial cells.

It is known that for an acute inflammatory response to occur, circulating neutrophils and/or monocytes must bind to and penetrate the vascular wall and access the site of injury. Several molecules have been implicated in this interaction, including a family of putative carbohydrate ligands and their receptors. A group of carbohydrate ligands for endothelial leukocyte adhesion molecule-1 (hereinafter ELAM-1) are disclosed in PCT/US91/05416 published 20 Feb. 1992 as WO 92/02527. The present invention provides a family of sulfated ligands.

An adhesion assay described in WO 92/02527 can be used to obtain a mixture of molecules which adhere to a selectin receptor which molecules can be sulfated. The invention encompasses those sulfated molecules and variations thereof which adhere to ELAM-1 receptors and/or other selectin receptors in this assay.

In accordance with the above description and the schematic diagrams of FIGS. 1 and 2, it can be seen how the sulfated ligands of the present invention can act as agonists in order to prevent and/or alleviate inflammation. Two other aspects of the invention can also be described by reference to FIGS. 1 and 2. More specifically, by including a compound such as a chlorate which prevents sulfation of the ligand, the ligand 4 would not be sulfated and therefore would have a configuration such that it would not adhere to the receptor 7 thereby preventing or alleviating inflammation. Further, after the ligand 4 was formed with sulfates thereon, a sulfatase could be added in order to remove the sulfates and cause the same effect. Since ligands which attach to LECAM-1 receptors also attach to ELAM-1 receptors, the same effect would be expected with respect to all types of selectin receptors. Accordingly, by combining sulfated ligand agonists of the invention with chlorates and sulfatases, a combined effect can be obtained with respect to preventing the adhesion between the white blood cells and the endothelial cells which combined effect can prevent and/or alleviate inflammation.

The above explanation of the in vivo function of ligands was established prior to the present invention. However, knowledge of such is useful in understanding of aspects of the present invention. Further, the above explanation made with reference to FIGS. 1 and 2 demonstrate the usefulness of the present invention. After our invention regarding sulfated ligands for selectins we found that other sulfated ligands have been investigated by others. For example, prior to the discovery that HEV ligands are, in fact, sulfated, the potential importance of sulfation for their function was suspected based on the potent ligand activity of a number of other sulfated carbohydrates (e.g., fucoidin, sea urchin egg jelly fucan, and sulfatide) for L-selectin (Stoolman, L. M., and Rosen, S. D., *J. Cell Biol.*, 96:722–729 (1983); Stoolman, L. M., Yednock, T. A., and Rosen, S. D., *Blood*, 70:1842–1850 (1987); Imai, Y., True, D. D., Singer, M. S., and Rosen, S. D., *J. Cell Biol.*, 111:1225–1232 (1990);. True, D. D., Singer, M. S., Lasky, L. A., and Rosen, S. D., *J. Cell Biol.*, 111:2757–2764 (1990)). Thereafter, although the importance of sulfation was not known, it was demonstrated that 3-sulfated Le$^x$/Le$^a$ (i.e., sulfated on 3-position of galactose), SGNL, and other sulfated structures are also capable of binding to L-selectin, apparently through specific interactions with its C-type lectin domain (Green, P. J., Tamatani, T., Watanabe, T., Miyasaka, M., Hasegawa, A., Kiso, M., Yuen, C. T., Stoll, M. S., and Feizi, T., *Biochem. Biophys. Res. Commun.*, 188:244–251 (1992); Suzuki, Y., Toda, Y., Tamatani, T., Watanabe, T., Suzuki, T., Nakao, T., Murase, K., Kiso, M., Hasegawa, A., Tadano-Aritomi, K., Ishizuka, I., and Miyasaka, M., *Biochem. Biophys. Res. Commun.*, 190:426–434 (1993); Needham, L. K., and Schnaar, R. L., *Proc. Natl. Acad. Sci. USA*, 90:1359–1363 (1993)). A review of these publications will show that none of the compounds disclosed within these publications has the sulfated structures of the compounds disclosed herein, and in particular do not possess the sulfated structures shown within structural formulas I(a)–(e) or II. The essential role of sulfation in the activity of these various carbohydrates caused us to focus our attention on the contribution of sulfation to GlyCAM-1 ligand activity. We have demonstrated (using chlorate as a metabolic inhibitor of sulfation) that sulfation of GlyCAM-1 (independent of its overall sialylation and fucosylation) is necessary for ligand activity (Imai, Y., Lasky, L. A., and Rosen, S. D., *Nature*, 361:555–557 (1993)). The sulfation requirement also holds for Sgp90/CD34. There are other examples of biologically significant recognition determinants that are defined by sulfate modifications of carbohydrates (Glabe, C. G., Grabel, L. B., Vacquier, V. D., and Rosen, S. D., *J. Cell Biol.*, 94:123–128 (1982); Kjellen, L., and Lindahl, U., *Ann. Rev. Biochem.*, 60:443–475 (1991); Rapraeger, A. C., Krufka, A., and Olwin, B. B., *Science*, 252:1705–1708 (1991); Roche, P., Debellé, F., Maillet, F., Lerouge, P., Faucher, C., Truchet, G., Dénarié, J., and Promém J. C., *Cell*, 67:1131–1143 (1991); Fiete, D., Srivastava, V., Hindsgaul, O., and Baenziger, J. U., *Cell*, 67:1103–1110 (1991); Cerami, C., Frevert, U., Sinnis, P., Takacs, B., Clavijo, P., Santos, M. J., and Nussenzweig, V., *Cell*, 70:1021–1033 (1992); Pancake, S. J., Holt, G. D., Mellouk, S., and Hoffman, S. L., *J. Cell Biol.*, 117:1351–1357 (1992); Guo, N. H., Krutzsch, H. C., Negre, E., Vogel, T., Blake, D. A., and Roberts, D. D., *Proc. Natl. Acad. Sci. USA*, 89:3040–3044 (1992); Needham, L. K., and Schnaar, R. L., *J. Cell Biol.*, 121:397–408 (1993)). These publications support the basic theory behind the present invention.

In order to utilize any of (1) the sulfated ligands, (2) the chlorates, or (3) the sulfatase enzyme the compound may be taken by itself or in combination with the others and formulated into a pharmaceutical formulation by combining any of the above compounds with a pharmaceutically acceptable excipient carrier. As regards the determination of the sulfated monosaccharide of an actual ligand of L-selectin, it is noted that they can be obtained by the mild acid hydrolysis of GlyCAM-1 (which may be metabolically labeled) followed by procedures including HPAEC. With respect to the sulfatase enzymes it should be pointed out that these enzymes can be extracted from natural sources or produced recombinantly. After extraction or recombinant production the sulfatase is purified using methodology known to those skilled in the art such as using high performance liquid chromatography. The sulfatase enzymes may be extracted from sources such as bacteria, fungi, plants, invertebrates, mammalian sources such as liver, kidney, brain, and leukocytes or endothelial cells. The sulfatase enzyme extracted and/or recombinantly produced is the enzyme which naturally removes sulfate moieties from natural ligands for L-selectins. The functionality of extracted or recombinantly produced enzymes can be readily confirmed by placing the enzyme in contact with sulfated ligands under appropriate conditions and determining the degree of removal of the sulfate moieties from the ligands.

The Effect of Sulfation on Ligands

L-selectin is a receptor present on all leukocytes and known to be involved in leukocyte attachment to endothelia. L-selectin functions as a calcium dependent lectin-like receptor (Lasky et al., *Cell*, 56:1045 (1989); Imai et al., *J. Cell Biol.*, 111:1225 (1990). Others (Imai et al., *J. Cell Biol.*, 113:1213 (1991)) have identified two endothelial ligands for L-selectin on lymph note high endothelial venules (HEV) as sulfated, fucosylated, and sialylated glycoproteins called Sgp50 and Sgp90 (sulfated glycoproteins of 50 kDa and 90 kDa).

Sgp50 has recently been molecularly cloned and shown to be a mucin-like glycoprotein with extensive O-linked carbohydrate chains. Sgp50 has been given the designation GlyCAM-1. Sgp90 is a HEV-specific glyco-form of CD34. Sialic acid on both Sgp50 and Sgp90 is required for their interaction with L-selectin. Several fortuitous carbohydrate-based inhibitors of L-selectin such as fucoidin and sulfatide are sulfated. Sulfate is required (but not sufficient) for binding activity (Imai et al., *Nature*, 361:555–557 (1993)). Examples exist where sulfate modifications of carbohydrate chains are essential for ligand activity (Lerouge et al., *Nature*, 344:781 (1990); Fiete et al., *Cell*, 67:1103).

Chlorate is a metabolic inhibitor of carbohydrate sulfation (Baeuerle and Huttner, *Biochem Biophys. Res. Comm.*, 141:870 (1986)). Accordingly, chlorate was used to test whether sulfation is required for the ligand binding activity of GlyCAM. When tests were carried out it was found that the presence of chlorate in organ cultures of lymph nodes substantially reduced (≈90%) incorporation of $^{35}S$—$SO_4$ into GlyCAM (and Spg90) and completely eliminated binding to L-selectin. Binding of GlyCAM to a sialic acid specific lectin (Limax agglutinin) or to a fucose-specific lectin (*Aleuria aurantia* agglutinin) was unchanged, indicating that sialylation and fucosylation of the molecule were not altered by the presence of chlorate.

By measuring incorporation of [$^3H$]-fucose into GlyCAM directly, it was confirmed that the level of fucosylation was not affected by chlorate. It was also demonstrated that chlorate did not affect the rate of synthesis of the protein core of GlyCAM. Taken together, we concluded that these results establish that sulfate is required for the interaction of GlyCAM (and Spg90) with L-selectin. In that sialyl-Lewis X (i.e., sLe$^x$) possesses ligand activity for L-selectin we have been able to deduce that the key carbohydrate chains of GlyCAM involve a sulfate-modification of a sLe$^x$-like oligosaccharide.

L-selectin (LAM-1, LECAM-1, TQ-1, Leu-8, DREG) on leukocytes participates in the initial attachment of lymphocytes, granulocytes, and monocytes to endothelium. Gallatin, W. M., Weissman, I. L. & Butcher, E. C., *Nature* 303:30–34 (1983); and Kishimoto, T. K., Jutila, M. A. & Butcher, E. C., *Proc. Natl. Acad. Sci. USA*, 87:2244–2248 (1990). On lymphocytes, it mediates binding to high endothelial venules (HEV) of lymph nodes during the process of lymphocyte recirculation. L-selectin, as a member of the selectin family of cell-cell adhesion proteins, Stoolman, L. M., *Cell*, 56:907–910 (1989), functions as a calcium-dependent lectin by recognizing carbohydrate-bearing ligands on endothelial cells. Yednock, T. A., Stoolman, L. M. & Rosen, S. D., *J. Cell Biol.*, 104:713–723 (1987) . Yednock, T. A., Butcher, E. C., Stoolman, L. M. & Rosen, S. D., *J. Cell Biol.*, 104:725–731 (1987) . Bevilacqua, M., et al., *Cell* 67:233–233 (1991) .

Inhibiting the Metabolic Sulfation of L-selectins

Slices of mouse lymph nodes were cultured with $^{35}S$-sulfate in the presence and absence of 10 mM chlorate. Detergent lysates were prepared and subjected to precipitation with several reagents that recognize GlyCAM-1. With a peptide antibody that binds to the polypeptide core of GlyCAM-1, the amount of labeled GlyCAM immunoprecipitated from the chlorate-treated culture was substantially reduced compared to that of the control culture. As determined by direct scintillation counting, chlorate treatment reduced the radioactivity immunoprecipitated by the peptide antibody to 12% of the control level. Culture in chlorate resulted in a similar reduction in the amount of $^{35}S$-sulfate precipitated by. Limax agglutinin (11.4% of control) and *Aleuria aurentia* lectin (13.7% of control), lectins that react with sialic acid and fucose, respectively. SDS-PAGE analysis demonstrated that this reduction was reflected in the commensurately reduced autoradiographic intensity of GlyCAM-1, although there were additional components in the precipitates. In contrast to these findings, LEC-IgG, the immunoglobulin chimera of L-selectin Watson, S. R., Imai, Y., Fennie, C., Geoffroy, J. S., Rosen, S. D. & Lasky, L. A., *J. Cell Biol.*, 110:2221–2229 (1990) failed to precipitate a detectable GlyCam-1 band from the chlorate-treated culture, whereas a strong band was seen in the control. Only a background level (0.9% of control) of radioactivity was measured in the precipitate from the chlorate-treated culture.

The simplest interpretation of these findings was that chlorate, as a consequence of its general inhibition of sulfation, reduced sulfate incorporation into GlyCAM-1 to about 10–15% of the control, as inferred from the ratio of counts precipitated by the peptide antibody. There was no apparent effect of chlorate on the overall sialylation or fucosylation of the molecule, since the reduction in Aleuria and Limax precipitated $^{35}S$—$SO_4$ counts closely paralleled the reduction in sulfate incorporation. However, the binding of LEC-IgG to GlyCAM, which represents the functional interaction of interest, was completely abrogated by culture in chlorate.

Other Effects Of Chlorate on L-selectin

To determine directly whether the fucosylation of GlyCAM-1 was affected by chlorate, $^3H$-fucose was employed as a metabolic precursor. The peptide antibody precipitated approximately the same number of cpm from detergent lysates obtained from the chlorate and control cultures; moreover, the autoradiographic intensity of the GlyCAM-1 component was comparable in both conditions. However, while LEC-IgG precipitated GlyCAM-1 in the control culture, LEC-IgG precipitated only a background level of counts (7% of control) from the chlorate-treated culture and there was no detectable GlyCAM-1.

To determine what effect chlorate had on the synthesis of the protein core of GlyCAM-1, the present inventors employed $^3H$-threonine as a metabolic label. When conditioned medium was analyzed, LEC-IgG precipitated a prominent GlyCAM-1 component from the control culture but did not react with any components when chlorate was present during the culture. With or without chlorate treatment, two antibodies against the core protein of GlyCAM-1 precipitated broad bands that ran at ≈50 K. With chlorate the distribution of the bands extended somewhat higher in the gel, possibly reflecting the effect of undersulfation on electrophoretic mobility. When lysates were immunoprecipitated with peptide antibodies, GlyCAM-1 was seen together with several lower molecular weight components. The same pattern was seen with the three independent antibodies. Importantly, culture in chlorate did not significantly alter either the intensity or pattern of the bands except for upward broadening of the highest molecular weight component. It is suspected that the lower molecular weight lysate components represent metabolic precursors to GlyCAM-1. If this speculation is correct, the absence of these components in conditioned medium would suggest that only the mature form of GlyCAM-1 is secreted.

Taken together, these results indicate that chlorate substantially inhibits the sulfation of GlyCAM-1 but allows biosynthesis of the protein core as well as sialylation and fucosylation of its carbohydrate chains to proceed normally. The complete loss of reactivity with LEC-IgG establishes the importance of sulfation for binding. As the O-linked carbohydrate chains of GlyCAM-1 have been shown to be sulfated and the polypeptide has only one potential tyrosine residue for sulfate addition, the present inventors have now concluded that the critical sulfates must be on the carbohydrate chains.

A variety of biological recognition phenomena depend on sulfate modifications of oligosaccharide chains. These include uptake of sulfated pituitary hormones by a hepatic reticuloendothelial receptor, Fiete, D., Srivastava, V., Hindsgaul, O. & Baenziger, J. U., *Cell*, 67:1103–1110 (1991) induction of root nodulation in certain legumes by a bacterially-derived sulfated oligosaccharide Roche, P., Debellé, F., Maillet, F., Lerouge, P., Faucher, C., Truchet, G., Dénarié, J., and Promé, J. C., *Cell*, 67:1131–1143 (1991) (see below), the interaction of heparin fragments with anti-thrombin, Kjellen, L. & Lindahl, U., *Ann. Rev. Biochem.*, 60:443–475

(1991) and the binding of basic FGF to cell surface heparan sulfate. The above-described results now extend this array of processes to a cell-cell recognition event by showing a sulfation requirement for GlyCAM-1, a biological ligand for L-selectin.

Previous work has demonstrated that E-selectin, Lowe, J. B., Stoolman, L. M., Nair, R. P., Larsen, R. D., Berhend, T. L. & Marks, R. M., *Cell*, 63:475–484 (1990). Phillips, M. L., Nudelman, E., Gaeta, F., Perez, M., Singhal, A. K., Hakomori, S. & Paulson, J. C., *Science*, 250:1130–1132 (1990). Walz, G., Aruffo, A., Kolanus, W., Bevilacqua, M. & Seed, B., *Science*, 250:1132–1135 (1990). Tiemeyer, M., Swiedler, S. J., Ishihara, M., Moreland, M., Schweingruber, H., Hirtzer, P. & Brandley, B. K., *Proc. Natl. Acad. Sci. (USA)*, 88:1138–1142 (1991) P-selectin, Polley, M. J., Phillips, M. L., Wayner, E., Nudelman, E., Singhal, A. K., Hakomori, S. & Paulson, J. C., *Proc. Natl. Acad. Sci. (USA)*, 88:6224–6228 (1991) and L-selectin Imai, Y., Lasky, L. A. and Rose, S. D., *Glycobiology*, 2:373–381 (1992); Foxall et al., *J. Cell Biol.*, 117:895–902 (1992), can all recognize the fucosylated and sialylated tetrasaccharide called sialyl Lewis X as well as related carbohydrates. The present inventors now disclose that the generation of a preferred biological ligand for each selectin involves distinctive modifications of a common carbohydrate structure, e.g., the sialyl Lewis X and/or sialyl Lewis A structure and specifically indicate that sulfation is an essential modification for Gly-CAM-1. An appropriate analogy may be provided by rhizobia-legume symbiosis, in which modified forms of a lipo-oligosaccharide function as nodulation-inducing signals, with host range defined by the nature of the modification. In the case of *Rhizobia melitoti*, sulfation of the core lipo-oligosaccharide determines the host specificity, whereas in other species different modifications are involved.

Identifying segments of GlyCAM-1

In order to define the nature of the sulfated monosaccharides on GlyCAM-1, we subjected the molecule to controlled acid hydrolysis. GlyCAM-1 was metabolically labeled with [$^{35}$S]-sulfate, [6-$^3$H]-galactose, [6-$^3$H]-glucosamine, [5,6-$^3$H]-fucose, or [2-$^3$H]-mannose in lymph node organ culture and purified from conditioned medium with an antibody directed to a peptide in the core protein. With all five of the radioactive labels employed, SDS-PAGE analysis of the isolated material showed that >95% of the radioactivity was concentrated in a diffuse band centered at 45 kDa. When $^{35}$SO$_4$-labeled GlyCAM was hydrolyzed in 0.2M H$_2$SO$_4$ (30 min at 100° C.), 85% of the counts eluted in the included volume of a P4 gel filtration column (FIG. 3A), indicating the presence of sulfate on low molecular weight fragments. Thin layer chromatography showed that the included material contained only trace levels of free sulfate. Thus, sulfate esters remained intact under these hydrolysis conditions. Hydrolysis of ([$^3$H]-Gal)- or ([$^3$H]-GlcN)-labeled GlyCAM-1 resulted in a similar division of counts between the included and void fractions on the same column (FIGS. 3B and 3C). With each of these labels, 15–25% of the counts were retained in the void volume (i.e., remained protein bound) after hydrolysis. However, when [$^3$H]-Fuc or [$^3$H]-Man was used for labeling, hydrolysis with as little as 0.1M H$_2$SO$_4$ released >98% counts in an included size-homogeneous fraction, which was uncharged and co-migrated with L-fucose (FIG. 4A). High pH anion exchange chromatography (HPAEC) confirmed that the included material derived from either ([$^3$H]-Man) or ([$^3$H]-Fuc)-labeled GlyCAM-1 was free n-fucose (FIG. 4B). Therefore, no evidence was obtained for the existence of sulfated forms of fucose.

Figure 5:
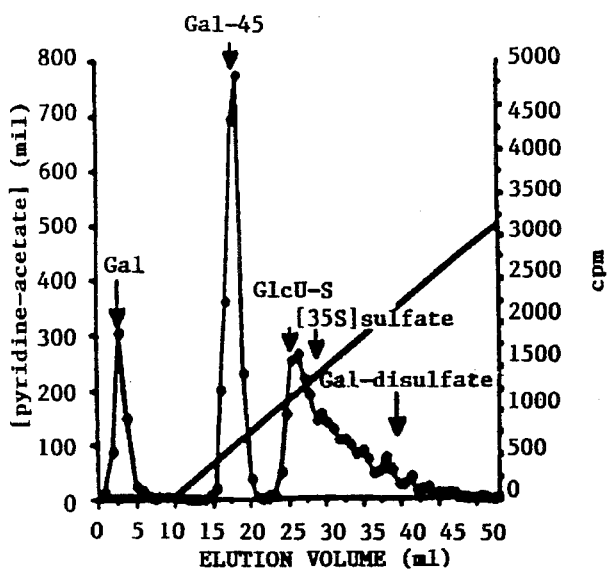
FIGS. 5A, 5B and 5C are graphs showing the anion exchange chromatography of hydrolysis products of GlyCAM-1. The P4-included fractions of the mild acid hydrolysates of GlyCAM-1, metabolically labeled with different precursors, were subjected to DEAE-Sepharose anion exchange chromatography 5A: $^{35}SO_4$; 5B: [$^3$H]-Gal; and 5C: [$^3$H]-GlcN. The diagonal lines indicate the concentration of eluting electrolyte (pyridine-acetate, pH 5). The elution positions of monosaccharide standards and $^{35}SO_4$ are indicated with arrows At the pH of the elution buffer, Gal-6S and sialic acid are singly charged whereas galactose disulfate and GlcU-S are doubly charged.
Figure 5:
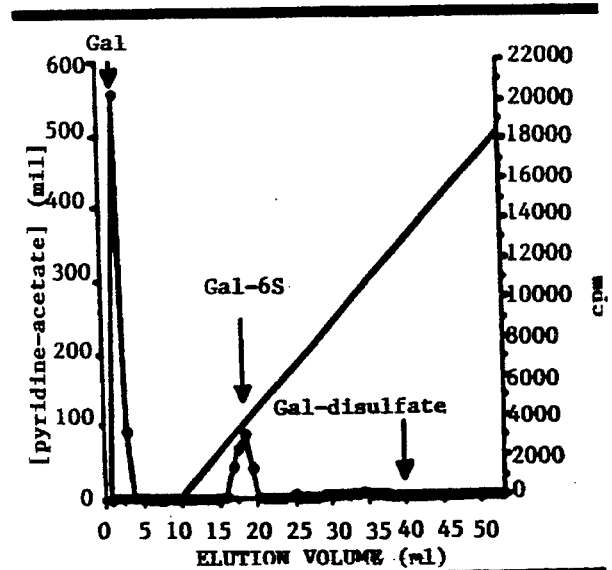
Figure 5:
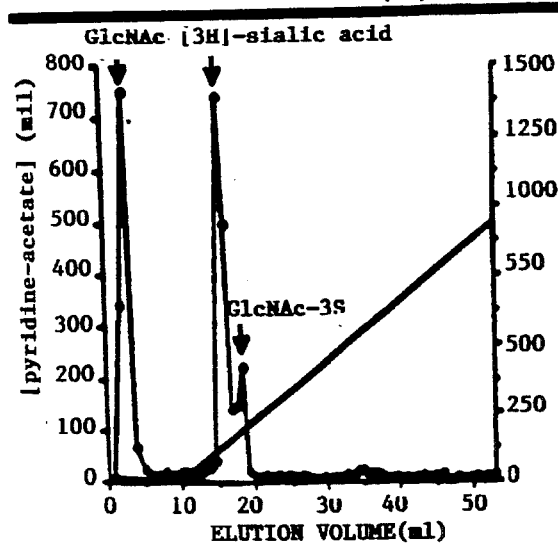

For further fractionation of the hydrolysis products obtained from ($^{35}$SO$_4$)-, ([$^3$H]-Gal)-, and ([$^3$H]-GlcN)-labeled GlyCAM-1, P4 fractions containing most (>90%) of the included counts were pooled and subjected to ion exchange chromatography on DEAE-Sepharose. A gradient elution with pyridine-acetate allowed separation of the fragments into unbound material (flow through), singly charged material (50–150 mM pyridine-acetate) and multicharged material (>200 mM pyridine-acetate). With $^{35}$SO$_4$ as the label, 12.5% of the counts were unbound (perhaps representing a zwitterionic sulfated amino sugar), 48% of the hydrolyzed material was singly charged, eluting as a sharp peak at 100 mM pyridine-acetate, while the multiply charged material comprised 40% of the counts and eluted as a poorly resolved succession of peaks between 200–400 mM pyridine-acetate (FIG. 5A). Material labeled with [$^3$H]-Gal or with [$^3$H]-GlcN produced qualitatively similar elution profiles, except that the multiply charged species see with $^{35}$SO$_4$ were not observed (FIGS. 5B and 5C). Because of the restricted labeling pattern of the multiply charged species, we focused our attention on the singly charged material.

Figure 6:
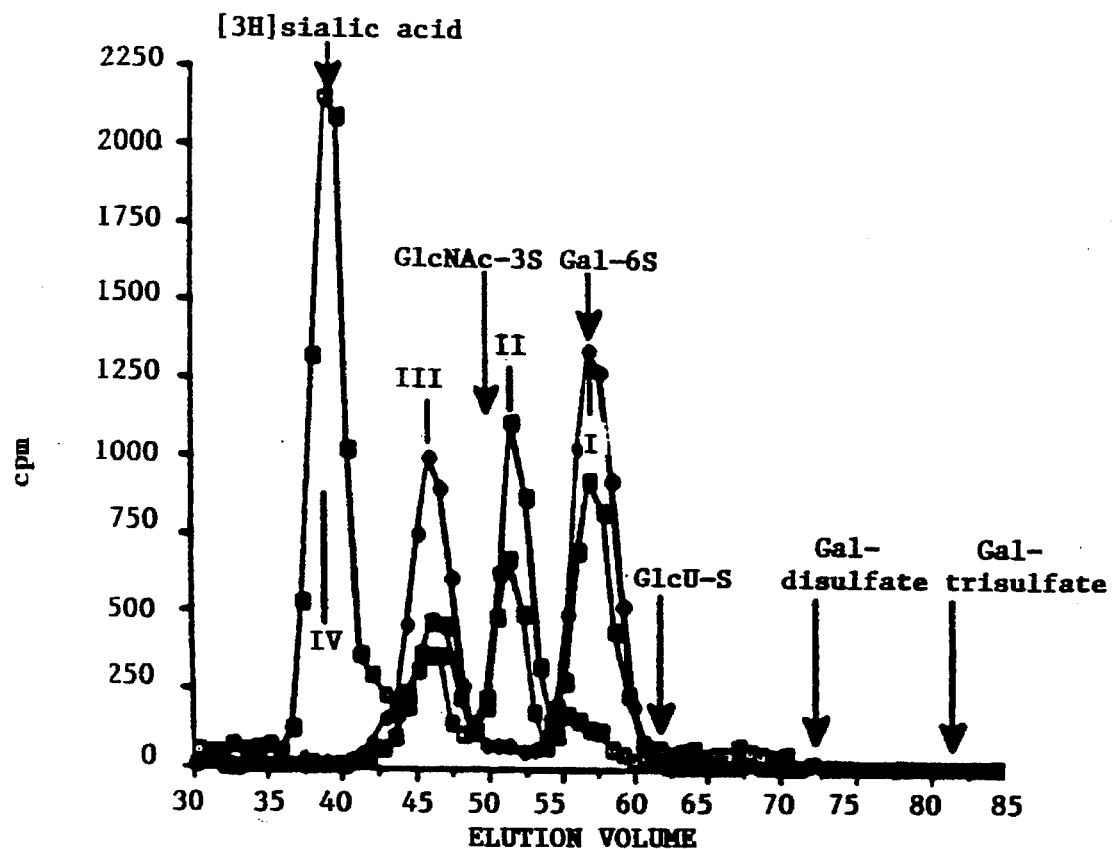
FIG. 6 is a graph showing a gel filtration analysis of singly charged components of hydrolyzed GlyCAM-1. The P4-included fractions of the mild acid hydrolysates of GlyCAM-1, metabolically labeled with different precursors, were subjected to DEAE-Sepharose anion exchange chromatography as in FIG. 4, and singly charged fractions were collected between 50 and 150 mM pyridine-acetate. These pools were subjected to rechromatography on a Bio-Gel P4 gel filtration column. ■: labeled with $^{35}So_4$; ♦: labeled with [$^3$H]-Gal; □: labeled with [$^3$H]-GlcN. The counts from the ([$^3$H]-GlcN)-labeled material were multiplied by four in this plot. Elution volume was defined as described in the legend to FIG. 3. The elution positions of monosaccharide standards are indicated with arrows.

Using gel filtration followed by DEAE chromatography, we isolated low molecular weight, singly charged hydrolysis products from GlyCAM-1 which had been labeled in parallel with $^{35}$SO$_4$, [$^3$H]-Gal, or [$^3$H]-GlcN. Upon rechromatography of these fractions on the P4 column, four well resolved peaks were obtained (FIG. 6). Peak I contained both the $^{35}$SO$_4$ and [$^3$H]-Gal labels. Peak II contained both the $^{35}$SO$_4$ and [$^3$H]-GlcN labels Peak III contained all three labels, while peak IV contained only the [$^3$H]-GlcN label. Due to metabolic interconversions, the tritium in [6-$^3$H]-GlcN will occur in GlcNAc, GalNAc, and sialic acid residues (Varki, A., *FASEB J.*, 5:226–235 (1991)). When ([$^3$H]-GlcN)-labeled GlyCAM-1 was treated with sialidase, the released counts co-migrated with peak IV on the P4 column. On this basis, peak IV was identified as sialic acid, although the exact form of sialic acid (among the extended set of naturally occurring variants) was not defined (Norgard, K. E., Moore, K. L., Diaz, S., Stults, N. L., Ushiyama, S., McEver, R. P., Cummings, R. D., and Varki, A., *J. Biol. Chem.*, 268:12764–12774 (1993)).

Peaks I, II and III were then subjected to strong acidic conditions (6M HCl, 100° C., 4 h) which hydrolyze all glycosidic bonds, sulfate esters, and N-acetyl bonds (Cummings, R. D., Merkle, R. K., and Stults, N. L., *Meth. Cell Biol.*, 32:141–183 (1989)). After evaporation to remove acid, the redissolved fractions were analyzed by HPAEC on a Dionex Carbopac I column and compared with authentic standards. All of the counts derived from ([$^3$H]-Gal)-labeled peak I co-eluted with Gal (FIG. 7A). All of the counts derived from ([$^3$H]-GlcN)-labeled peak II co-eluted with GlcN, while none of the radioactivity co-eluted with GalN (FIG. 7B). All of the counts derived from ([$^3$H]-Gal)-labeled peak III co-eluted with galactose. Finally, all of the counts derived from ([$^3$H]-GlcN)-labeled peak III co-eluted with GlcN and none co-eluted with GalN (FIG. 7C). These results, together with the observed peak profiles on the P4 column (FIG. 6), indicate that peak I contains Gal-sulfate, peak II contains GlcN(Ac)-sulfate, and peak III contains a monosulfated form of Gal→GlcN(Ac) or GlcN(Ac)→Gal.

For further characterization of peaks II and III, these fractions were subjected to solvolysis (50 mM HCl in MeOH, 5% H$_2$O, 37° C., 24 h) to remove sulfate. About 70% of both ([$^3$H]-Gal)-labeled peak III and ([$^3$H]-GlcN)-labeled peak II did not bind to the DEAE column after this treatment. By HPAEC analysis, the unbound fraction derived from the hydrolysis of ([$^3$H]-GlcN)-labeled peak II co-eluted with GlcNAc rather than GlcN, establishing that peak II contains GlcNAc—O—SO$_3$— and not GlcN—SO$_3$— (FIG. 8A). By a similar HPAEC analysis, the unbound product derived from the hydrolysis of ([$^3$H]-Gal)-labeled peak III co-eluted with Galβ1→4GlcNac but not with Galβ1→3GlcNAc or Galβ1→6GlcNAc (FIG. 8B). Digestion of this unbound material with exo-β-galactosidase (jack bean) converted it quantitatively into [$^3$H]-Gal (FIG. 8C). These results establish that peak III is a monosulfated form (or forms) of N-acetyllactosamine (Galβ1→4GlcNAc).

Figure 9:
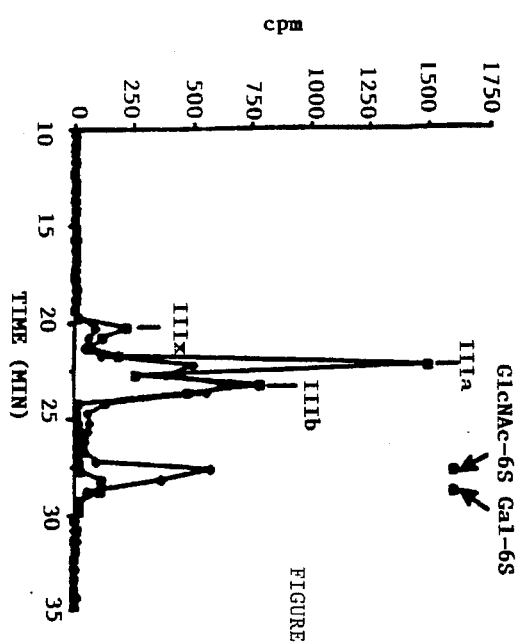
FIGS. 9A, 9B, 9C and 9D are graphs showing the high pH anion exchange chromatography of sulfated peaks I, II, and III. (9A) HPAEC profile of peak I labeled either with $^{35}SO_4$(□) or [$^3$H]-Gal(♦)-elution program 2 (cf. experimental section). (9B) HPAEC profile of peak II labeled either with $^{35}SO_4$ (□) or [$^3$H]-GlcN(♦)-elution program 1. (9C) HPAEC profiles of $^{35}SO_4$-labeled peak III (□) and a jack bean exo-β-galactosidase digested sample (♦)-elution program 2. (9D) HPAEC profiles of ($^{35}SO_4$)-labeled peak III(□) and a hydrolysed sample (0.1M $H_2SO_4$, 1 h, 100° C.) (♦)-elution program 2. The elution times of the carbohydrate and sulfate standards are indicated with arrows.
Figure 9:
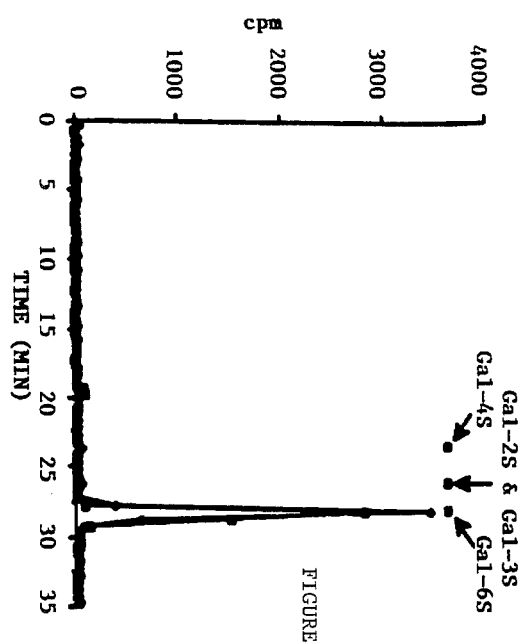
Figure 9:
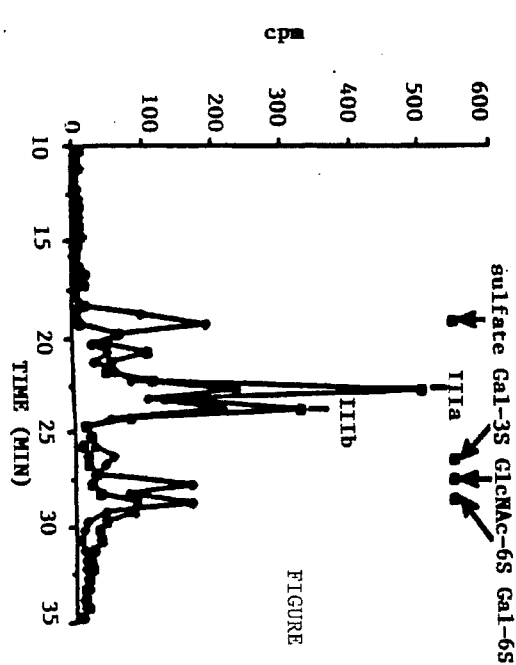
Figure 9:
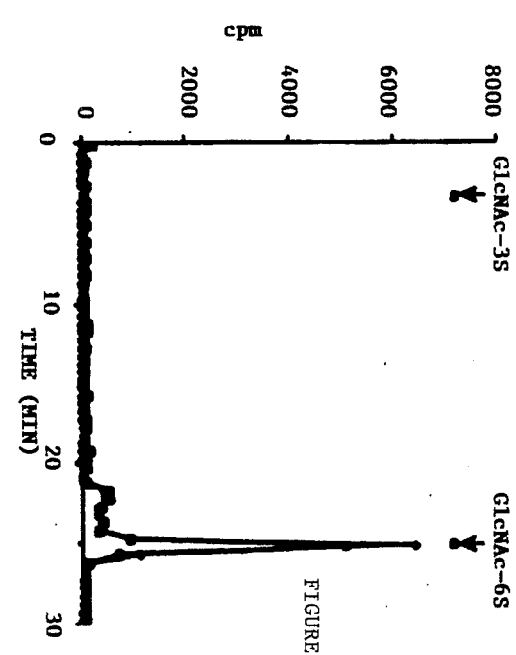

To determine the linkage positions of the sulfate esters in peaks I, II and III, these fractions were compared to standards by HPAEC analysis (Carbopac I, NaOAc gradient in 150 mM NaOH). All of the counts in both ([$^3$H]-Gal)-labeled peak I and ($^{35}$SO$_4$)-labeled peak I co-eluted with Gal-6S, which was clearly resolved from Gal-2S, Gal-3S and Gal-4S (FIG. 9A). The majority of the counts (95%) in ([$^3$H]-GlcN)-labeled peak II co-eluted with GlcNAc-6S, which was well resolved from GlcNAc-3S (FIG. 9B). From these results and the preceding analysis, peaks I and II are identified as Gal-6S and GlcNAc-6S, respectively.

Chemical hydrolysis of ($^{35}$SO$_4$)-labeled peak III (0.1M H$_2$SO$_4$, 60 min, 100° C.) gave rise to both Gal-6S and GlcNAc-6S as well as some free $^{35}$SO$_4$ (FIG. 9D) These results, together with the assignment of the N-acetyllactosamine core structure described above, reveal that peak III is a mixture of Galβ1→4GlcNAc-6-OSO$_3$— and —O$_3$SO-6-Galβ1→4GlcNAc. In support of this conclusion, peak III was fractionated by HPAEC into two major peaks (designated IIIa and IIIb) comprising about 90% of the applied counts. The peak profiles were identical for material labeled with $^{35}$SO$_4$ (FIGS. 9C and 9D), [$^3$H]-Gal or [$^3$H]-GlcN (data not shown). Treatment with jack bean exo-β-galactosidase converted ($^{35}$SO$_4$)-labeled peak IIIa into a species that co-migrated with GlcNAC-6S, identifying peak IIIa as Galβ1→4GlcNAc-6-OSO$_3$— (FIG. 8C). Peak IIIb was identified as —O$_3$SO-6-Galβ1→4GlcNAc based on its resistance to cleavage by exo-β-galactosidase, which is predicted to be inactive towards sulfate-substituted galactosides (Green, E. D., and Baenziger, J. U., *J. Biol. Chem.*, 263:25–35 (1988); Spiro, R. G., and Bhoyroo, V. D., *J. Biol. Chem.*, 263:14351–14358 (1988)).

Use and Administration

The compounds of the invention such as (1) various chlorates, (2) sulfatases, and (3) sulfated ligands can be administered to a subject in need thereof to treat a patient, i.e., prophylactically preventing inflammation or relieving it after it has begun. The sulfatases as well as chlorates such as sodium or potassium chlorate and/or sulfated ligands are preferably administered with a pharmaceutically acceptable carrier, the nature of the carrier differing with the mode of administration, for example, oral administration, usually using a solid carrier and I.V. administration a liquid salt solution carrier. The formulation and/or means of administration will also vary depending on whether a chlorate, sulfatase or a sulfated ligand is being administered, e.g., a sulfatase is an enzyme which would not generally be administered orally but would be administered by I.V.

The desired formulation can be made using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the sulfated ligand molecules and chlorates directly in transdermal formulations with permeation enhancers such as DMSO. Other topical formulations can be administered to treat dermal inflammation.

A therapeutically effective amount is an amount of sulfated ligand molecules which will bind to a substantial proportional number of the L-selectin receptor so that inflammation can either be prevented or ameliorated. Alternatively, a therapeutically effective amount of a chlorate will prevent sulfation of natural ligands in large enough numbers so as to prevent or alleviate inflammation. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose of sulfatases, chlorates and/or sulfated ligand agonists to be administered, it must be kept in mind that one may not wish to completely block all of the selectin receptors. In order for a normal healing process to proceed, at least some of the white blood cells or neutrophils must be brought into the tissue in the areas where the wound, infection or disease state is occurring. The amount of the sulfatases, chlorates and/or sulfated ligands administered as blocking agents must be adjusted carefully based on the particular needs of the patient while taking into consideration a variety of factors such as the type of disease that is being treated.

It is believed that the sulfatases, chlorates and/or sulfate ligands of the present invention can be used to treat a wide range of diseases, including diseases such as rheumatoid arthritis, asthma, adult respiratory distress syndrome, sarcoidosis, hypersensitivity pneumonitis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of sulfatases, chlorates and/or sulfated ligands might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The white blood cells possess the LECAM-1 receptors. The receptors adhere to ligand molecules on the surface of activated endothelial cells. The ligand molecules may be induced to the surface of the endothelial cells by activation. Large numbers of white blood cells are quickly captured and brought into the tissue surrounding the affected area, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. This is most preferably done by local injection of sulfatases, chlorates and/or sulfated ligand agonists to the area subjected to trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, sulfatases, chlorates, and/or sulfated ligand agonist of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A variety of different respiratory diseases exhibit symptoms which are aggravated by inflammation and all aspects of the present invention can be used in the treatment of such diseases in order to alleviate and/or prevent the aggravation of such symptoms. This is preferably done by the topical pulmonary administration of the sulfated ligand agonists, sulfatases and/or chlorates of the invention. Such compounds can be topically delivered to the passages of the lung surface. Aerosol formulations may be delivered by the use of conventional metered dose inhalers (MDIs). By formulating any or all of the sulfated ligand agonists, sulfatases or chlorates in combination with a suitable propellant and delivering the formulation via an MDI, relief from pulmonary inflammation can be obtained in a very short period of time.

Sulfated ligand agonists, sulfatases and/or chlorate of the invention are preferably administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the chlorate and/or sulfated agonist adequate to achieve the desired state in the subject being treated.

The various sulfatases, chlorates and sulfated ligand agonists of the present invention can be used by themselves, with each other, or in combination with pharmaceutically acceptable excipient materials as described above. Further, the ligand compounds of the invention can be made as conjugates wherein the sulfated ligands are linked in some manner to a label, e.g., fluorescent, radioactive and enzyme labels. By forming such conjugates, the ligand compounds of the invention act as biochemical delivery systems for the label so that a site of inflammation can be detected.

Sulfated ligand agonists of the invention could also be used as laboratory probes to test for the presence of a selectin in a sample. Such probes are preferably labeled.

EXAMPLES

The following examples are put forth so as to provide those of ordinary skill in the art with a complete disclosure and description of methodologies carried out in order to demonstrate the importance of sulfate groups present on L-selectin ligands with respect to their interaction and/or binding with L-selectin receptors. These examples are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, molecular weight is weight average molecular weight, temperature is in degrees Centigrade, and pressure is at or near atmospheric.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, preferred methods and materials are now described. All publications mentioned herein are incorporated herein by reference.

Example 1

Inhibition of GlyCAM-1 sulfation eliminates its interaction and/or binding with L-selectin. This conclusion was reached when lymph nodes were metabolically labelled in organ culture with (a) [$^{35}$-S]-sulfate or (b) [$^3$-H]-fucose in the presence or absence of chlorate and detergent lysates were subjected to precipitation with L-selectin chimera (LEC-IgG), a rabbit anti-Sgp50 peptide antibody (antipeptide 2), rabbit preimmune serum, *Limax flavus* agglutinin (sialic acid specificity), or *Aleuria aurantia* agglutinin (AAA; fucose specific). The apparent molecular weight of [$^3$-H]-fucose-labelled GlyCAM-1 was slightly larger in the presence of chlorate, probably because the reduced sulfation retards electrophoretic mobility.

Pooled mesenteric and peripheral lymph nodes from ICR mice (80 mg wet weight per condition) were incubated with (a) 250 uCi of [$^{35}$-S]-sodium sulfate (ICN) or (b) 250 uCi of [5,6 $^3$-H]-L-fucose (ICN) in the presence or absence of 10 mM Na chlorate (Aldrich) in 0.5 ml of RPMI-1640 with 25 mM HEPES (1/10 sulfate concentration) for 4 h at 37° C. Tissue was extracted with 1.2 ml of 2% Triton X-100 (Boehringer Mannheim) in Dulbecco's PBS containing 1 mM PMSF (Sigma), 1% (v/v) aprotinin (Sigman), 10 ug/ml of pepstatin (Boehringer Mannheim) and 0.02% NaN$_3$ (lysis buffer) as described previously[11]. The lysates were boiled 3 min and the supernatants were precleared with 100 ul of Protein A Sepharose (Zymed) overnight. Aliquots of the precleared supernatants were added to 10 ul beads of LEC-IgG-Protein A Sepharose Beads (30 ug LEC-IgG per 10 ul beads), rabbit anti-peptide 2-Protein A beads (10 ul serum per 10 ul beads), rabbit preimmune serum-Protein A beads (10 ul serum per 10 ul beads), Limax flavus agglutinin-Sepharose beads (20 ug protein per 10 ul beads), or Aleuria aurantia agglutinin-Sepharose beads (10 ug protein per 10 ul beads), and incubated for 4 h at 4° C. on a rocker. The beads were washed in the lysis buffer (6 times), and the 1/14 aliquots of beads were saved for direct counting by a scintillation counting and the remainder of beads were solubilized in Laemmli sample buffer (without beta mercaptoethanol) and run by on a 10% acrylamide gel (nonreducing condition) with fluorography employing ENHANCE (New England Nuclear). Molecular weight markers (BioRad) were phosphorylase B (97.4 K), BSA (66.2 K), ovalbumin (45 K), carbonic anhydrase (31 K), soybean trypsin inhibitor (21.5 K). LEC-IgG and antiserum were coated on Protein A-Sepharose beads by rocking overnight at 4° C. Lectin beads were prepared by coupling Limax agglutinin (Calbiochem) and AAA (Boehringer Mannheim) to CNBr-activated Sepharose 4B (Sigman). Miller, R., *Meth. Enzymol.* 138:527–536 (1987).

Example 2

Inhibition of GlyCAM-1 sulfation eliminates its interaction and/or binding with L-selectin. This conclusion was reached when aliquots of the same precipitates of Example 1, labelled with (a) [$^{35}$-S]-sulfate or (b) [$^3$-H]-fucose in the presence or absence of chlorate were subjected to scintillation counting. The results indicate the percent counts obtained in the presence of chlorate as compared to the absence of chlorate. The values for anti-peptide 2, Limax, and AAA were essentially the same, reflecting the overall reduction in sulfation. In an independent experiment, the corresponding values were: 6% (for LEC-IgG), 35.6% (for anti-peptide 2), 35.3% (for Limax).

Example 3

Inhibition of GlyCAM-1 sulfation eliminates its interaction and/or binding with L-selectin. This conclusion was reached when lymph nodes were labeled with L-[3-$^3$H]-threonine in the presence or absence of chlorate. Conditioned medium (a) or detergent extracts (b) were subjected to precipitation with LEC-IgG, rabbit anti-Sgp50 anti-peptide antibodies (anti-peptide 1, 2, 3), or rabbit preimmune serum.

Mouse lymph nodes were labeled with 750 uCi of L-[3-$^3$H] threonine (Amersham) in 0.5 ml of threonine free-1/10 sulfate concentration-RPMI 1640 containing 25 mM HEPES for 4 h at 37° C. in the absence or the presence of 10 mM-sodium chlorate. Detergent lysates were boiled, precleared and subjected to precipitation with the indicated reagent as described in Example 1. Conditioned media were precleared and precipitated in parallel. The bead-bound material was analyzed on SDS-PAGE under reducing conditions with fluorography. In the anti-peptide antibody lanes, the ≈50 K component was compressed by the immunoglobulin heavy chain.

Example 4

Metabolic labeling of murine lymph nodes

For metabolic labeling (Imai, Y., Lasky, L. A., and Rosen, S. D., *Nature*, 361:555–557 (1993), axillary, brachial, cervical, and mesenteric lymph nodes were dissected from five ICR mice, diced with a razor-blade, and incubated in 1 ml of RPMI-1640, supplemented with penicillin (100 units/ml) and streptomycin (0.1 mg/ml). The tissue was cultured for 4 h (37° C.) in the presence of D-[6-$^3$H]-galactose, D-[6-$^3$H]-glucosamine, D-[2-$^3$H]-mannose (at 0.5 mCi/ml, all from Du Pont New England Nuclear, Boston, Mass.), L-[5,6-$^3$H]-fucose, or Na$_2^{35}$SO$_4$ (at 1 mCi/ml, both from ICN, Costa Mesa, Calif.). Labeling with $^{35}$SO$_4$ was carried out in a mixture of 90% sulfate-free RPMI-1640 and 10% standard RPMI-1640. Conditioned medium was collected from the culture and cleared by centrifugation for 5 min at 10,000× g.

Immunoprecipitation of GlyCAM-1

All steps were carried out at 4° C. GlyCAM-1 was immunoprecipitated from the conditioned medium by the addition of 20 μl of protein A-Sepharose 4B (Zymed, So. San Francisco, Calif., 2.5 mg recombinant protein A/ml gel) derivatized with rabbit polyclonal antibody directed to the peptide CKEPSIFREELISKD (pep2) from the deduced GlyCAM-1 protein core (Lasky, L. A., Singer, M. S., Dowbenko. D., Imai, Y., Henzel, W. J., Grimley, C., Fennie, C., Gillett, N., Watson, S. R., and Rosen, S. D., *Cell*, 69:927–938 (1992)). The matrix was washed five times in Tris-buffered saline (TBS: 10 mM Tris-HCl pH 7.4, 150 mM NaCl) and bound ligand was eluted from the matrix by the addition of 200 μl TBS containing free pep2 (1 mg/ml). One tenth of the preparation (20 μl) was subjected to SDS gel electrophoresis on a 10% polyacrylamide gel according to Laemmli (Laemmli, U. K., *Nature*, 227:680–685 (1970)), followed by fluorography using Enhance (New England Nuclear).

Mild acid hydrolysis of GlyCAM-1

The above ligand preparation was treated with 0.2M H$_2$SO$_4$ (final volume 250 μl), overlayed with clear mineral oil (Sigma), and incubated at 100° C. for 30 min.

Thin layer Chromatography

After neutralization of the hydrolysate with 50 μl of 2N NH$_4$OH, two 1 μl-aliquots were applied to a 100 mm×50 mm silica gel-coated glass plate (60 F254, Merck, Darmstadt, Germany). Two 0.5 μl aliquots of 1 mM Na$^{35}$SO$_4$ solution (5000 cpm each) were then applied to the same plate, with one aliquot overlayed into the hydrolyzed material and the second in a separate lane. The plate was developed in n-BuOH/N,N-dimethylformamide (DMF)/1M sodium borate pH 9, 50:20:25, followed by fluorography with Enhance spray (New England Nuclear).

Initial fractionation of mild acid hydrolysate by gel filtration

The neutralized hydrolysate was combined with 50 μl of 2.5% hemoglobin (Sigma) in 0.1M pyridine-acetate pH 5.4 and loaded onto a column of Biogel P4 (200–400 mesh, Bio-Rad Laboratories, Richmond, Calif., 112 cm×1 cm, bed volume=88 ml) in pyridine-acetate (0.1M, pH 5.4). The column was eluted at 22° C. with the same pyridine-acetate buffer at a rate of 5 ml/h, and 30-drop fractions (0.83–0.87 ml) were collected. A 40 μl sample of each fraction was mixed with 5 ml Ultima Gold scintillation cocktail (Packard, Downers Grove, Ill.) and counted in a Beckman LS-8000 liquid scintillation counter, Elution volume is given relative to the first appearance of hemoglobin (void volume) which occurred at 28.4 ml.

Carbohydrate standards employed in gel filtration analysis

The P4 column was calibrated with carbohydrate standards that were obtained as follows. [$^3$H]-Sialic acid was obtained by sialidase treatment (*Arthrobacter ureafaciens*, Calbiochem, La Jolla, Calif.; 0.3 units per ml, pH 5.5, 30 min, 37° C.) of GlyCAM-1 metabolically labeled with [$^3$H]-glucosamine. N-Acetylglucosamine-3-sulfate (GlcNAc-3S, sodium salt) and galactose-6-sulfate (Gal-6S, sodium salt) were from Sigma. Glucuronic acid monosulfate (GlcU-S, mixture of isomers) was prepared by treatment of glucuronic acid with two molar equivalents of $SO_3$-trimethylamine (Westerduin, P., Willems, H. A., and van Boekel, C. A. A., *Tetrahedron Lett.*, 31:6915–6918 (1990)) in anhydrous DMF (4 h, 25° C.) under an inert atmosphere. The reaction was neutralized with saturated $NaHCO_3$ and the product was purified by chromatography on DEAE-Sephadex (Aldrich) eluting with a linear gradient of 0–2M pyridine-acetate (pH 5.4). The pyridinium salt was converted to the sodium salt by passage over Bio-Rad 50W-X4 resin ($Na^+$ form). Galactose-disulfate and galactose-trisulfate (mixtures of isomers) were prepared by treatment of galactose with five molar equivalents of $SO_3$-trimethylamine in anhydrous DMF (6 h, 40° C.), followed by neutralization with saturated $NaHCO_3$. The products were purified by anion exchange chromatography, and the resulting pyridinium salts were converted to the corresponding sodium salts as described above. All three synthetic derivatives were characterized by negative fast atom bombardment ($FAB^-$) mass spectrometry. GlcNAc-3S was detected in the fractions eluted from the P4 column with the Elson Morgan reaction (Reissig, J. L., Strominger, J. L., and Leloir, L. F., *J. Biol. Chem.*, 217:959–966 (1955)). The galactose-sulfates were detected with the phenol-sulfuric acid assay (Dubois, M., Gilles, K. A., Hamilton, J. K., Rebers, P. A., and Smith, F., *Anal. Chem.*, 28:350–356 (1956)). GlcU-S was detected with the carbazole reaction (Bitter, T., and Muir, H. M., *Anal. Biochem.*, 4:330–334 (1956)).

Anion-exchange chromatography of P4-included fraction of mild acid hydrolysate

The fractions eluting from the P4 column after 42 ml (after 35 ml for ([$^3$H-GlcN)-labeled GlyCAM-1) were pooled and lyophilized. The residue was dissolved in 200 µl of water and loaded onto a DEAE-Sepharose column (Sigma, acetate form, 80 mm×5 mm, bed volume=1.6 ml) equilibrated with 2 mM pyridine-acetate (pH 5.0). The column was eluted with 8.5 ml of 2 mM pyridine-acetate, followed by 85 ml of a 2–1000 mM linear gradient of pyridine-acetate (pH 5.0). Fractions (30-drops, ~0.85 ml) were collected and a 30 µl sample of each fraction was counted as above. The column was calibrated with the indicated standards. Fractions eluting from the DEAE-Sepharose column between 50 and 150 mM pyridine-acetate (singly charged material) were pooled and lyophilized.

Gel filtration of singly charged fraction

The preparation of single charged fragments obtained above was redissolved in 200 µl of water and fractionated by gel filtration on the P4 column. Fractions were pooled as follows: peak I (55–60 ml), peak II (49–54 ml), peak III (43–48 ml), and peak IV (36–42 ml). Pooled fractions were lyophilized and the residues were redissolved in 20 µl of water and stored at −80° C. until further analysis.

Total hydrolysis of sulfated carbohydrates

Hydrolysis of the sulfated carbohydrates to yield desulfated and deacetylated monosaccharide units was accomplished by heating samples of peaks I, II and III in 6M HCl (4 h, 100° C.). After hydrolysis, samples were evaporated repeatedly from water and redissolved in water for monosaccharide compositional analysis by high pH anion exchange chromatography (HPAEC).

Desulfation

Peaks II and III were desulfated (without concomitant deacetylation) by incubation in 50 mM methanolic HCl/5% $H_2O$ (24 h, 36° C). After desulfation, the residues were concentrated, redissolved in water, and loaded onto a DEAE-Sepharose column (80 mm×5 mm, bed volume=1.6 ml) equilibrated in 2 mM pyridine-acetate (pH 5.0). The column was eluted with 2 mM pyridine-acetate (pH 5.0) and uncharged material was recovered as the flow-through fraction. The unbound products were lyophilized and redissolved in water for further analysis.

β-Galactosidase digestions

Radiolabeled oligosaccharide fragments were reacted with jack bean exo-β-galactosidase (0.25 units/ml, Sigma) in 20 mM $NaH_2PO_4$ (buffered to pH 3.5 with acetic acid) in a final volume of 50 µl for 18 h at 37° C. The digests were then subjected to analysis by HPAEC.

Partial hydrolysis of ($^{35}SO_4$)-labeled peak III

The material from $^{35}SO_4$-labeled peak III was reacted with 0.1M $H_2SO_4$ in a final volume of 10 µl (overlayed with mineral oil) for 1 h at 100° C. After neutralization with 2N $NH_4OH$, the hydrolysate was analyzed by HPAEC.

High pH anion exchange chromatography (HPAEC)

Peaks I, II and III and their respective products of desulfation, enzymatic digestion, and hydrolysis were analyzed by HPAEC using a Carbopac PA1 column (Dionex, Sunnyvale, Calif., 250 mm×4 mm). Each sample was injected in 25 µl of water. Elution conditions (flow rate 1 ml/min) were as follows. For analysis of total hydrolysates and desulfated peak II: 20 mM NaOH isocratic; for desulfated peak III and its β-galactosidase digest: 100 mM NaOH isocratic; for sulfated peak II: 150 mM NaOH for 4 min, followed by a linear gradient of 0–250 mM NaOAc in 150 mM NaOH over 20 min (program 1); for sulfated peak I, peak III, β-galactosidase digest and partial hydrolysate of peak III: 50 mM NaOAc in 150 mM NaOH for 5 min, followed by a linear gradient of 50–850 mM NaOAc in 150 mM NaOH over 30 min (program 2). Standards were used at 0.4 mM and analyzed with pulsed amperometric detection. Radiolabeled products were detected by collecting 0.5 min fractions followed by liquid scintillation analysis as described above.

Carbohydrate standards employed in HPLC analysis

Gal-6S, GlcNAc-3S, GlcNAc, Galβ1→3GlcNAc, Galβ1→4GlcNAc (N-acetyllactosamine, LacNAC), and Galβ1→6GlcNAc were from Sigma. Gal-4S and GlcNAc-6S were from V-Labs (Covington, La.). Gal-3S was obtained by hydrolysis of bovine sulfatides (Matreya Inc., Pleasant Gap, Pa.) in 0.1M $H_2SO_4$ (30 min, 100° C.). Gal-2S was synthesized from 12,3,4,6-tetra-O-acetyl-α-D-galactopyranose (Helferich, B., and Zimer, J., *Ber.*, 2604–2611 (1962)) using a procedure based on that of Peat et al. (Peat, S., Bowker, D. M., and Turvey, J. R., *Carbohydr. Res.*, 7:225–231 (1968)). The product was characterized by $^1$H NMR spectroscopy and by $FAB^-$ mass spectrometry. Neutral monosaccharide standards (an equimolar mixture of Fuc, GalN, GlcN, Gal, Glc, and Man) were from Dionex.

The above examples 1–3 demonstrate that the presence of sulfate on GlyCAM-1 is essential for its avid interaction with L-selectin. Example 4 particularly identifies the sulfate modifications of GlyCAM-1. Since conventional analysis of the GlyCAM-1 carbohydrates has so far been hampered by the limited quantities of available ligand, we employed radioactive tracer techniques that have been used widely in the sequencing of glycoprotein oligosaccharides (Varki, A., *FASEB J.*, 5:226–235 (1991); Cummings, R. D., Merkle, R. K., and Stults, N. L., *Meth. Cell Biol.*, 72:141–183 (1989); Shilatifard, A., Merkle, R. K., Helland, D. E., Welles, J. L., Haseltine, W. A., and Cummings, R. D., *J. Virol.*, 67:943–952 (1993); Maemura, K., and Fukuda, M., *J. Biol. Chem.*, 267:24379–24386 (1992)). The oligosaccharides of GlyCAM-1 were metabolically labeled in organ culture with $^{35}SO_4$ and a panel of tritiated carbohydrate precursors to allow specific introduction of label into defined monosaccharide units. The analysis relied on the use of hydrolysis conditions that released sulfated oligosaccharides without the significant cleavage of sulfate esters.

In light of the previously demonstrated ligand activity of fucoidin and egg jelly coat fucan (fucose-4-sulfate rich polysaccharides) for L-selectin (Stoolman, L. M., and Rosen, S. D., *J. Cell Biol.*, 96:722–729 (1983); Imai, Y., True, D. D., Singer, M. S., and Rosen, S. D., *J. Cell Biol.*, 111:1225–1232 (1990)), we initially suspected that sulfated fucose might be present in GlyCAM-1. Prior work has shown that mild acid hydrolysis (0.15M $H_2SO_4$, 30 min, 100° C.) liberates sulfated fucose (fucose-3-sulfate and fucose-3,4-disulfate) from a sea cucumber chondroitin sulfate (Viera, R. P., Mulloy, B., and Mourao, P. A. S., *J. Biol. Chem.*, 266:13530–13536 (1991)). However, hydrolysis of GlyCAM-1 under these conditions released all of the [$^3$H]-Man or [$^3$H]-Fuc labeled counts as neutral fucose, arguing against sulfation of fucose residues in this ligand. The [2-$^3$H]-mannose precursor is known to be incorporated into glycoproteins both as mannose and fucose units (Varki, A., *FASEB. J.*, 5:226–235 (1991)). The exclusive incorporation of all mannose label into GlyCAM-1 as fucose indicates the complete absence of mannose in the GlyCAM-1 carbohydrates. This result further substantiates that the oligosaccharide chains of GlyCAM-1 are all O-linked, as previously indicated by the complete resistance of the ligand to N-glycanase digestion (Imai, Y., Singer, M. S., Fennie, C., Lasky, L. A., and Rosen, S. D., *J. Cell Biol.*, 113:1213–1221 (1991)).

Mild acid hydrolysis of ($^{35}SO_4$)-labeled GlyCAM-1 yielded fragments with a heterogenous range of size and charge. We concentrated our analysis on P4-included fractions carrying a single charge.

The structural identification of the singly charged hydrolysis products was accomplished as follows. Fragments labeled with $^{35}SO_4$ and $^3$H-sugars were subjected to further hydrolysis, desulfation, and enzymatic digestion to characterize the monosaccharide components. Sulfate ester linkage positions were assigned by HPAEC analysis with authentic standards. The results of Example 4 identified —$O_3$SO-6-Gal, GlcNAc-6-$OSO_3$—, Galβ1→4GlcNAc-6-$OSO_3$— and —$O_3$SO-6-Galβ1→4GlcNAc as components of GlyCAM-1. The results provide no evidence for the presence of galactose-3-sulfate on GlyCAM-1, although various Gal-3S containing carbohydrates have ligand activity for L-selectin (Green, P. J., Tamatani, T., Watanabe, T., Miyasaka, M., Hasegawa, A., Kiso, M., Yuen, C. T., Stoll, M. S., and Feizi, T., *Biochem. Biophys. Res. Commun.*, 188:244–251 (1992); Suzuki, Y., Toda, Y., Tamatani, T., Watanabe, T., Suzuki, T., Nakao, T., Murase, K., Kiso, M., Hasegawa, A., Tadano-Aritomi, K., Ishizuka, I., and Miyasaka, M., *Biochem. Biophys. Res. Commun.*, 190:426–434 (1993)). GlcNAc-6S has been identified in a wide assortment of glycoconjugates which include the glycosaminoglycan chains of keratan sulfate (Rodén, L., *In The Biochemistry of Glycoproteins and Proteoglycans*, p. 267–372 (1980) (W. J. Lennarz, ed.) Plenum Press: New York), viral envelope glycoproteins of type I human immunodeficiency virus (Shilatifard, A., Merkle, R. K., Helland, D. E., Welles, J. L., Haseltine, W. A., and Cummings, R. D., *J. Virol.*, 67:943–952 (1993), chicken adipose lipoprotein, glycoproteins of bovine large vessel endothelial cells (Roux, L., Holojda, S., Sundblad, G., Freeze, H. H., and Varki, A., *J. Biol. Chem.*, 263:8879–8889 (1988)), bovine and human thyroglobulin (Spiro, R. G., and Bhoyroo, V. D., *J. Biol. Chem.*, 263:14351–14358 (1988), and a rhizobial nodulation factor (Roche, P., Debellé, F., Maillet, F., Lerouge, P., Faucher, C., Truchet, G., Dénarié, J., and Promé, J. C., *Cell*, 67:1131–1143 (1991)). Gal-6S has been found in keratan sulfates (Rodén, L., *In The Biochemistry of Glycoproteins and Proteoglycans*, p. 267–372 (W. J. Lennarz, ed.) Plenum Press: New York (1980)), human tracheobronchial mucins (Mawhinney, T. P., Adelstein, E., Morris, D. A., Mawhinney, A. M., and Barbero, G. J., *J. Biol. Chem.*, 267:2994–3001 (1986), rat salivary mucins together with GlcNAc-6S (Slomiany, B. L., Piotrowski, J., Nishikawa, H., and Slomiany, A., *Biochem. Biophys. Res. Commun.*, 157:61–67 (1988) and recombinant human tissue plasminogen activator (Pfeiffer, G., Stirm, S., Geyer, G., Strube, K.-H., Bergwerff, A. A., Kamerling, J. P., and Vliegenthart, J. F. P., *Glycobiology*, 2:411–418 (1992). In keratan sulfate and plasminogen activator, Gal-6S occurs on N-acetyllactosamine units, as is the case for the structures identified in Example 4.

The functional requirements for sialic acid, sulfate and probably fucose must be included in any model for the recognition determinants on GlyCAM-1. One possibility is that individual O-linked chains contain either sialic acid-based or sulfate-based determinants. The individual chains would be recognized by separate lectin domains of oligomeric L-selectin or may form a combined epitope for a single lectin domain (Norgard, K. E., Moore, K. L., Diaz, S., Stults, N. L., Ushiyama, S., McEver, R. P., Cummings, R. D., and Varki, A., *J. Biol. Chem.*, 268:12764–12774 (1993)). Removal of either sialic acid or sulfate would greatly reduce the overall avidity of the interaction between the ligand and L-selectin.

Preferred ligands have sulfation and sialylation on the same O-linked chain forming an L-selectin recognition site, e.g. as a sulfated sLe$^x$-like structure. Previously, we observed that all ($^{35}SO_4$)-labeled O-linked chains released from GlyCAM-1 by beta elimination are able to bind to a sialic acid-specific lectin (Limax agglutinin) (Imai, Y., and Rosen, S. D., *Glycoconjugate J.*, 10:34–39 (1993)). Thus, sulfation does not occur without sialylation on individual chains. In addition to structure I(c) above, the general structures I(d) and I(e) shown below identify possible positions for sialylation and fucosylation on chains bearing —$O_3$SO-6-Galβ1→4GlcNAc and Galβ1→4GlcNAc-6-$OSO_3$—.

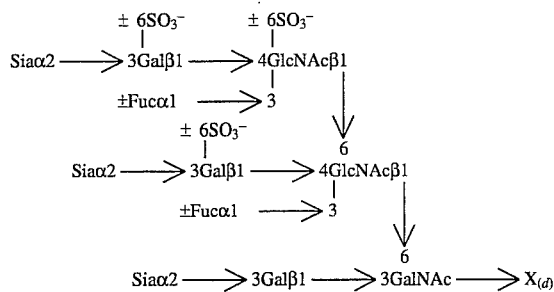

I(d)

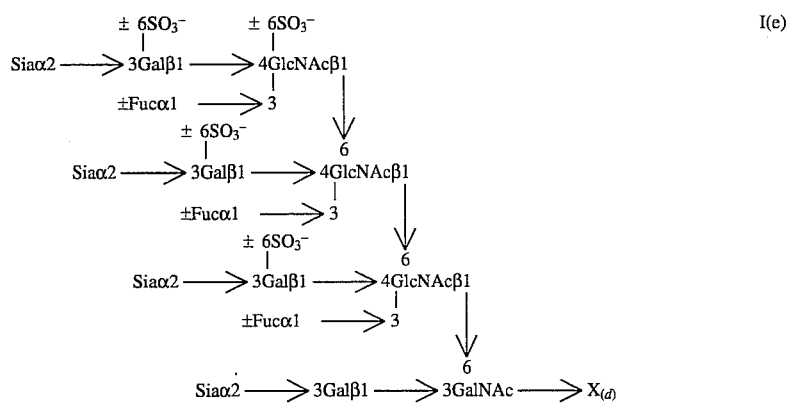

I(e)

wherein $X_{(d)}$ and $X_{(e)}$ are defined as per X of structure $X_{(a)}$ above.

Sialylation on the 3-position of galactose and fucosylation on the 3-position of GlcNAc are preferred positions. Single galactose residues may be modified by both 3-sialylation and 6-sulfation and single GlcNAc residues may be modified by both 6-sulfation and 3-fucosylation.

Example 5

Analysis of hydrolysis fragments of metabolically-labeled GlyCAM-1

GlyCAM-1 was metabolically labeled in lymph node organ culture with $^{35}SO_4$, and a panel of tritiated carbohydrate precursors as described in Example 1 above. Mild hydrolysis conditions were used that released sulfated oligosaccharides without the generation of free sulfate. Low molecular weight and singly-charged fragments, obtained by a combination of gel filtration and anion exchange chromatography, were analyzed. The identification of the fragments relied on the use of a variety of radiolabeled sugar precursors (R. D. Cummings, R. K. Merkle and N. L. Stults, in *Methods in Cell Biology*. (Academic Press, 1989), vol. 32, and A. Varki, *FASEB J.*, 5:226–235 (1991)) and subjected the singly charged fractions to further chemical and enzymatic hydrolysis with the eventual assignment of structures by high pH anion exchange chromatography analysis with authentic standards. The sulfated constituents of GlyCAM-1 were identified as $-O_3SO$-6-Gal, GlcNAc-6-$OSO_3^-$, Galβ1→4GlcNAc-6-$OSO_3^-$ and $^-O_3SO$-6-Galβ1→4GlcNAc.

Example 6

Reactivity of GlyCAM-1 with lectins

Previous work has established that sulfate (Y. Imai, L. A. Lasky and S. D. Rosen, *Nature*, 361:555–557 (1993)) and sialic acid and probably fucose (Y. Imai, L. A. Lasky and S. D. Rosen, *Glycobiology*, 4:373–381 (1992)) are essential for the avid interaction of GlyCAM-1 with L-selectin. GlyCAM-1 was analyzed with respect to sialic acid and fucose substitutions of the sulfated structures obtained in the hydrolysis of GlyCAM-1 (see Example 5 above). For this purpose, a group of lectins with defined carbohydrate specificity was used to examine their binding to GlyCAM-1. Both normal and undersulfated GlyCAM-1 with or without enzymatic desialylation and/or defucosylation was tested.

($^3$H-Gal)-labeled GlyCAM-1 was produced in mouse lymph node organ cultures as described in Examples 1–4 above. Undersulfated GlyCAM was generated by organ culture of murine lymph nodes in medium containing 10 mM Na-chlorate, a known inhibitor of sulfation. GlyCAM-1 was isolated from the conditioned media by immunoprecipitation with an antibody to a peptide sequence in the core protein of GlyCAM-1 (CAM02 Ab), as described in Examples 1–4 above. While GlyCAM incorporated about the same [$^3$H]-galactose activity in the presence or absence of chlorate ($2 \times 10^6$ cpm from 0.25 mCi input), the incorporation of [$^{35}$S]-sulfate was suppressed in the presence of chlorate to 10% of that in the control ($0.16 \times 10^6$ vs. $1.75 \times 10^6$ cpm, 0.5 mCi input). Desialylation of GlyCAM-1 was accomplished in all cases by treatment with *Arthrobacter ureafacens* sialidase (1.75 units/ml) in 120 mM Na acetate, pH 5.5 (18 h 37° C.).

The lectins used in the analysis were as follows:

WGA: wheat germ agglutinin (H. Lis and N. Sharon, *Ann Rev BioChem*, 52.:35–67 (1986)); recognizes sialic acid (Sia) and terminal GlcNAc*. eluant: GlcNAc

*Sugar abbreviations used above: Fuc, fucose; Gal, galactose; GalNAc, N-acetylgalactosamine; GlcNAc, N-acetylglucosamine; Sia, sialic acid (encompasses all naturally occurring variants of this sugar).

AAA: *Aleuria aurantia* agglutinin (H. Debray and J. Montreuil, *Carbo. Res.*, 185:15–20 (1989)); recognizes α1–2, α1–3, and α1–6 linked fucose, eluant: fucose TJA-1: *Trichosanthes japonica* agglutinin (K. Yamashita, K. Umetsu, T. Suzuki and T. Ohkura, *Biochemistry*, 31:11647–50 (1992)) recognizes Siaα2-6Galβ1–4GlcNAc or $SO_4$-6-Galβ1–4GlcNAc. eluant: lactose SNA: *Sambucus nigra* (elderberry bark) agglutinin (K. Yamashita, K. Umetsu, T. Suzuki and T. Ohkura, *Biochemistry*, 31:11647–50 (1992), and N. Shibuya et al., *J. Biol .Chem.*, 262:1569–1601 (1987)); recognizes Siaα2–6GalNAc, Siaα2-6-Galβ1–4GlcNAc and $SO_4$-6-Galβ1–4GlcNAc. eluant: lactose MAA: *Macckia amurensis* agglutinin (R. N. Knibbs, I. J. Goldstein, R. M. Ratcliffe and N. Shibuya, *J. Biol Chem.*, 262:83–88 (1991)); recognizes Siaβ2–3Galβ1–4GlcNAc. eluant: lactose PNA: peanut agglutinin (H. Lis and N. Sharon, *Ann Rev Biochem.*, 55, 35–67 (1986)); recognizes Galβ1–3GalNAc. eluant: lactose.

LEA: *Lycopersicon esculentum* agglutinin (tomato lectin) (R. D. Cummings, R. K. Merkle and N. L. Stults, in *Methods in Cell Biology* (Academic Press, 1989), vol. 32); binds to (β1–4GlcNAc) oligomers with no requirement that GlcNAc is consecutive. Eluant: N-acetylglucosamine.

As an additional precipitating reagent, an antibody-to the C-terminal peptide of GlyCAM-1 (CAM05 Ab) was also used. The eluant for CAM05 Ab was 0.1M glycine-HCl, 0.2M NaCl, 0.25% Triton X-100, pH 3.0. Binding was expressed as % of total cpm input.

GlyCAM-1 preparations were agitated with immobilized lectin (0.2 ml matrix gel per ml, derivatization: 1–2 mg lectin per ml gel) in phosphate buffered saline (PBS) containing 0.1% BSA 0.01% $NaN_3$ for hr at 4° C., then matrices were centrifuged, washed four times with PBS containing 0.25% Triton X-100 and eluted with 100 mM specific eluant in PBS containing 0.25% Triton X-100. The activity in the eluates was then determined by liquid scintillation counting.

The results of the lectin precipitation analysis were as shown in Table I below.

TABLE I

| Presence of | | Lectin Precipitation Analysis % of CPM Precipitated | | | | | | |
|---|---|---|---|---|---|---|---|---|
| Sia | $SO_4$ | TJA-1 | SNA | MAA | WGA | AAA | PNA | CAM05 Ab |
| + | + | 8.2 | 11.2 | 4.2 | 86.7 | 61.5 | 1.5 | 58.7 |
| + | − | 1.6 | 3.6 | 28.9 | 82.8 | 81.2 | 2.9 | 88.8 |
| − | + | 63.0 | 35.0 | 0.2 | 14.1 | 64.0 | 20.8* | 73.3 |
| − | − | 3.1 | 0.2 | 0.4 | 24.3 | 69.5 | 38.9 | 85.5 |

*Low signal due to loss of material

The results of the above experiments on lectin precipitation demonstrated:

(a) Desialylation with Arthrobacter sialidase exposed a cryptic binding site for both TJA-1 and SNA. This site depended on sulfation since the desialylated and undersulfated material failed to bind to these two lectins.

(b) Undersulfation of GlyCAM-1 exposed a cryptic MAA-binding activity, which depended on sialylation.

(c) Desialylation exposed a cryptic PNA-binding activity. Binding to PNA was not markedly influenced by presence or absence of sulfate.

The hydrolysis analysis of metabolically labeled GlyCAM-1 together with the lectin precipitation analysis strongly supported that Siaα2–3($SO_4$-6)Galβ1–4GlcNAc was present within a major capping structure for GlyCAM-1 carbohydrate chains. The results with PNA suggested that the GlyCAM-1 carbohydrates contained a sialylated T-antigen like structure (i.e., Siaα2–3Galβ1–3GalNAc).

Example 7

Sequential exoglycosidase digestion of GlyCAM-1

Normal or undersulfated GlyCAM-1, labeled with [$^3$H]-Gal, was isolated from conditioned medium of lymph nodes by immunoprecipitation with CAM02 Ab conjugated to protein A-agarose as described above. The isolated ligand was digested, with or without prior desialylation, with the following enzymes:

(1) exo-β1–4galactosidase (from Diplococcus, Boehringer Mannheim, #1088718) at 0.1 units/ml in 50 mM Na-cacodylate pH 6.0 for 48 h at 37° C.; or (2) exo-β1–4 galactosidase (from Diplococcus, Boehringer Mannheim, #1088718) at 0.1 units/ml plus α1–3/4 fucosidase (Takara Biochemicals, Tokyo) (K. Maemura and M. Fukuda, *J Biol Chem.*, 267:24379–24386 (1992)) at 0.1 milliunits/ml in 50 mM Na-cacodylate pH 6.0 for 48 h at 37° C.

The digests were loaded on Sephadex G-25 gel filtration columns (270 mm×8 mm in PBS, 0.25% Triton X-100). Columns were eluted with PBS, 0.25% Triton X-100 and 0.5 ml fractions were collected. Entire fractions were counted for [$^3$H]-radioactivity. The undigested material eluted in the void volume (4–5 ml) while liberated [$^3$H]-Gal was included in the column and eluted 2.5–4 ml after the void volume.

The results with [$^3$H]-Gal were as shown in Table II below.

TABLE II

| Digestion of [$^3$H] Gal. Labelled GlyCAM-1 | | | |
|---|---|---|---|
| Presence of | | Percent Release of [$^3$H] Gal. Labelled by GlyCAM-1 | |
| Sia | $SO_4$ | Exo β-Gal-ase | Exo β1-Gal-ase + Exo α1¾ Fuc-ase |
| + | + | 0 | 0 |
| + | − | 0 | 0 |
| − | + | 4 | 12 |
| − | − | 10 | 35 |

Normal or undersulfated GlyCAM-1, metabolically labeled with [$^3$H]-fucose was digested with α1–3/4 fucosidase (Takara Biochemicals, Tokyo) at 0.1 milliunits/ml in 50 mM Na-cacodylate, with or without concomitant desialylation. Liberated [$^3$H]-Fuc was determined by gel filtration analysis as described above for galactose. The results with [$^3$H]-Fuc were as shown in Table III below.

TABLE III

| Digestion of [$^3$H]-fucose labelled GlyCAM-1 | | |
|---|---|---|
| Presence of | | Percent Release of [$^3$H]-Fuc from |
| Sia | $SO_4$ | GlyCAM-1 by α 1¾ fucosidase |
| + | + | 0 |
| + | − | 0 |
| − | + | 70 |
| − | − | 85 |

The ability of desialylated ([$^3$H]-Gal)-labeled GlyCAM-1, undersulfated or normal, with or without treatment with the α1–3/4 fucosidase to bind to AAA or LEA (tomato lectin) was determined. See Example 6 above for the binding specificity of AAA and LEA and for the assay conditions.

The results of the analysis were as shown in Table IV below.

TABLE IV

Binding of ([³H]-Gal)-GlyCAM-1

| Presence of | | | Percent Binding of ([³H]-Gal)-GlyCAM-1 | |
|---|---|---|---|---|
| Sia | Fucose | SO₄ | AAA | LEA |
| – | + | + | 60 | 5.2 ± 0.2 |
| – | + | – | 80 | 13.9 ± 0.4 |
| – | – | + | 23.4 | 47.6 ± 3.7 |
| – | – | – | 10.1 | 43.8 ± 1.8 |

The results of experiments in Tables II, III and IV demonstrated the following:

1. About 35% of all galactose in GlyCAM-1 was in a penultimate position relative to sialic acid and was linked β1→4 to GlcNAc. This result followed from the fact that undersulfated, desialylated and defucosylated material released 35% of its [³H]-Gal counts upon treatment with β1–4 exo-galactosidase (Table II). All of this galactose was normally sialylated, judging from the complete lack of activity of β1–4 exo-galactosidase on GlyCAM-1 unless the ligand was desialylated. This was true whether or not the molecule was undersulfated.

2. Fucose is α1→3 linked to GlcNAc. This result followed from the actions of the α1–3/4 fucosidase which: (1) accentuated the release of [³H]-Gal counts from GlyCAM-1 by β1–4 exo-galactosidase (Table II); (2) directly released [³H]-Fuc counts from GlyCAM-1 (Table III); and (3) increased the binding of GlyCAM-1 to LEA, which is known to bind to β1–4 linked GlcNAc (Table IV). Since the 4-position of GlcNAc is involved in the linkage to Gal (i.e., Galβ1–4GlcNAc), fucose must be bound in a α1–3 linkage to GlcNAc. From the data of Table II, it was estimated that ≈70% of the first GlcNAc was substituted with fucose.

3. The presence of sulfation greatly hindered the release of [³H]-Gal counts from GlyCAM-1 upon treatment with β1–4 exo-galactosidase (Table II). This result provided further evidence with the α1–4 linked galactose residues were substituted with sulfate, probably at the 6-position. From the effect of exo-β-galactosidase on the release of [³H]-Gal counts from defucosylated, sulfated GlyCAM-1 vs. defucosylated, undersulfated GlyCAM-1, it was estimated that ≈60% of the terminal β1–4 galactose residues were substituted with sulfate.

proposed structure for capping groups of GlyCAM-1 carbohydrate:

The data presented above on the analysis of hydrolysis products of metabolically labeled GlyCAM-1, binding of GlyCAM-1 to lectins of defined carbohydrate specificity, and the use of glycosidases to degrade the oligosaccharide chains of GlyCAM-1 demonstrated that a typical carbohydrate chain of GlyCAM-1 consisted of a sialylated T antigen of formula II below, i.e. Siaα2–3Galβ1–3GalNAc-O-Ser/Thr that was extended at the 6-position of the Ser/Thr-linked GalNAc with an unknown number of N-acetyllactosamine units, which were capped at the nonreducing terminus by a 6-sulfated, sialyl Lewis X structure (i.e., terminal galactose substituted by both α2–3 linked sialic acid and sulfation at the 6-position. Some of the GlcNAc units were also sulfated at their 6-positions. In the above structures I(a)–I(e), ± denotes that the modification may or may not be present at the indicated position. The exact form of sialic acid, among the many possible occurring natural variants of this sugar (R. Schauer, *Trends in Biochem Sci.*, 10:357–360 (1985)) is not specified. The capping groups for GlyCAM-1 carbohydrate claims are shown in structures I(a) and I(b), and specific structures of capping groups in more complete form are shown above in structures I(c), I(d) and I(e).

Example 8

Experiments were conducted to determine the binding of Sgp50 and Spg90 to antibody MECA-79 m Ab. Results of these experiments demonstrated that binding of Spg50 and Spg90 to MECA-79 m AB depends on the sulfation of these ligands.

The various aspects of the present invention have been shown and described herein in what is considered to be the most practical, and preferred embodiments. It is recognized, however, that departures may be made therefrom which are within the scope of the invention, and that obvious modifications will occur to one skilled in the art upon reading this disclosure.

We claim:

1. A sulfated, sialylated, fucosylated O-linked oligosaccharide compound of formula I(a):

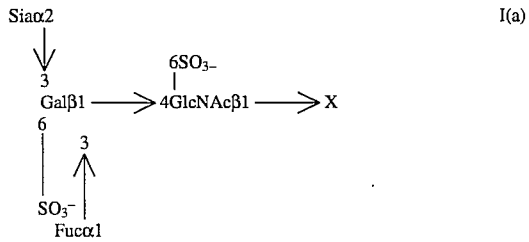

wherein GlcNAc is N-acetylglucosamine, Gal is galactose, Sia is sialic acid, Fuc is fucose and X is a moiety connected to the 1-position of GlcNAc selected from the group of —OH, a detectable label and a pharmaceutically active drug.

2. A pharmaceutical composition comprising a pharmaceutically acceptable carrier and a therapeutically effective amount of a compound of claim 1.

3. A method of treating inflammation comprising administering to a patient in need of such a therapeutically effective amount of the composition of claim 2.

4. The method as claimed in claim 3, wherein the composition is administered by injection.

5. The method of claim 3, wherein the composition is administered by inhalation.

6. A compound of structural formula I(c):

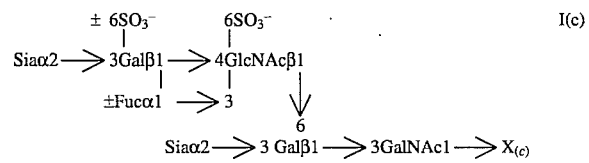

wherein $X_{(c)}$ is a moiety connected to GalNAc at the 1-position selected from the group of —OH, a detectable label and a pharmaceutically active drug.

7. A pharmaceutical composition comprising a pharmaceutically acceptable excipient carrier and a therapeutically effective amount of a compound of claim 6.

8. A method of treating inflammation comprising administering to a patient in need of such a therapeutically effective amount of the composition of claim 7.

9. A compound of structural formula I(d):

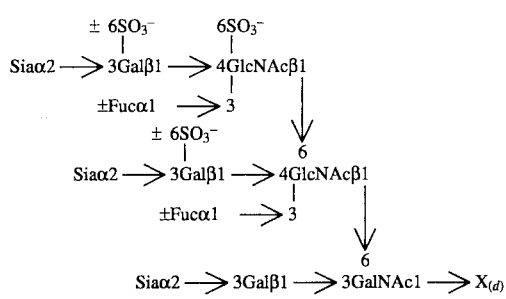

wherein $X_{(d)}$ is a moiety connected to GalNAc at the 1-position selected from the group of —OH, and detectable label and a pharmaceutically active drug.

10. A pharmaceutical composition comprising a pharmaceutically acceptable excipient carrier and a therapeutically effective amount of a compound of claim 9.

11. A method of treating inflammation comprising administering to a patient in need of such a therapeutically effective amount of the composition of claim 10.

12. A compound of structural formula I(e):

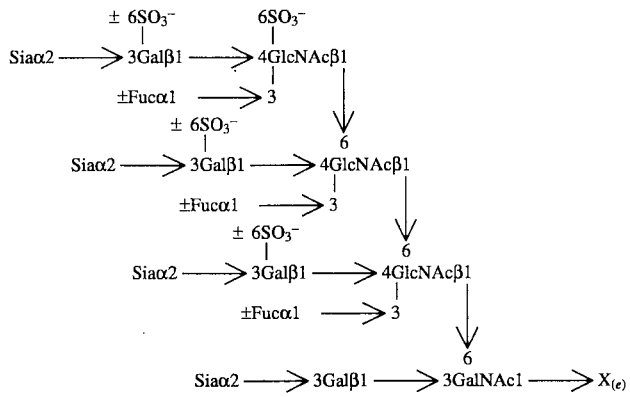

wherein $X_{(e)}$ is a moiety connected to GalNAc at the 1-position selected from the group of —OH, a detectable label and a pharmaceutically active drug.

13. A pharmaceutical composition comprising a pharmaceutically acceptable excipient carrier and a therapeutically effective amount of a compound of claim 12.

14. A method of treating inflammation comprising administering to a patient in need of such a therapeutically effective amount of the composition of claim 13.

15. A sulfated, fucosylated O-linked oligosaccharide compound having the structural formula II;

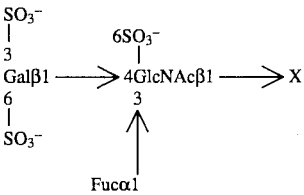

wherein GlcNAc is N-acetylglucosamine, Gal is galactose, Sia is sialic acid, Fuc is fucose and X is a moiety connected to the 1-position of GlcNAc selected from the group of —OH, a detectable label and a pharmaceutically active drug.

16. A pharmaceutical composition comprising a pharmaceutically acceptable carrier and a therapeutically effective amount of a compound of claim 15.

17. A method of treating inflammation comprising administering to a patient in need of such a therapeutically effective amount of the composition of claim 16.

18. A compound having a structure selected from the group consisting of:

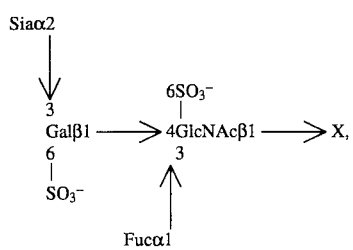

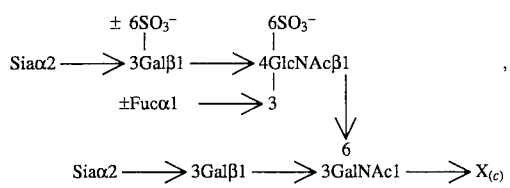

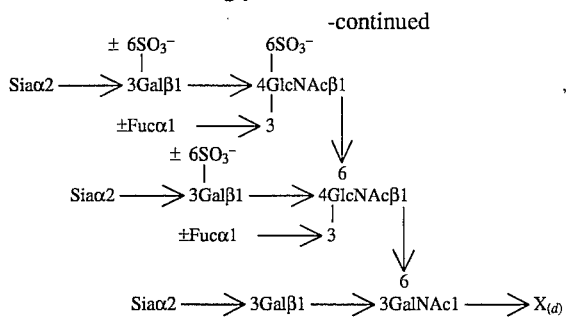
I(d)
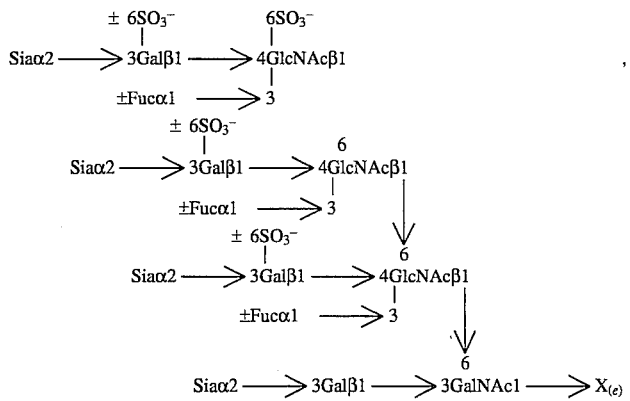
I(e)
and
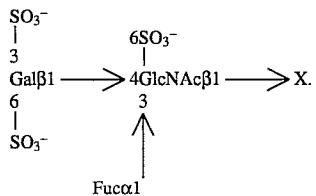
II
* * * * *

UNITED STATES PATENT AND TRADEMARK OFFICE
CERTIFICATE OF CORRECTION

PATENT NO. : 5,489,578
DATED : 2/6/96
INVENTOR(S) : Steven D. Rosen

It is certified that error appears in the above-indentified patent and that said Letters Patent is hereby corrected as shown below:

On The Title Page:
Item 22 should read May 2, 1995

Signed and Sealed this

Twenty-seventh Day of August, 1996

Attest:

BRUCE LEHMAN

Attesting Officer   Commissioner of Patents and Trademarks

UNITED STATES PATENT AND TRADEMARK OFFICE

CERTIFICATE OF CORRECTION

PATENT NO. : 5,489,578

DATED : Feb. 6, 1996

INVENTOR(S) : Stephen D. Rosen and Stefan Hemmerich

It is certified that error appears in the above-identified patent and that said Letters Patent is hereby corrected as shown below:

```
On the title page, filing date should read --May 2, 1995--
```

Signed and Sealed this

Tenth Day of February, 1998

Attest:

BRUCE LEHMAN

*Attesting Officer*      *Commissioner of Patents and Trademarks*